US012694956B2

(12) United States Patent
Frieder et al.

(10) Patent No.: US 12,694,956 B2
(45) Date of Patent: Jul. 28, 2026

(54) SYSTEM FOR PROVIDING VALIDATION OF DEEP LEARNING BASED PRESCRIPTION EFFICACY

(71) Applicant: Georgetown University, Washington, DC (US)

(72) Inventors: Ophir Frieder, Chevy Chase, MD (US); Dinesh Maheshwari, Mountain View, CA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 312 days.

(21) Appl. No.: 18/311,743

(22) Filed: May 3, 2023

(65) Prior Publication Data

US 2024/0371480 A1 Nov. 7, 2024

(51) Int. Cl.
*G16H 10/60* (2018.01)

(52) U.S. Cl.
CPC .................................. *G16H 10/60* (2018.01)

(58) Field of Classification Search
CPC .............................. G16H 10/60; G16H 50/70
See application file for complete search history.

(56) References Cited

U.S. PATENT DOCUMENTS

| | | | | |
|---|---|---|---|---|
| 10,937,531 B1 * | 3/2021 | Wang | ...................... | G16H 80/00 |
| 11,610,688 B2 * | 3/2023 | Ng | .......................... | G16H 10/60 |
| 12,488,882 B2 * | 12/2025 | Todd | .................... | G06Q 30/016 |
| 2009/0265316 A1 * | 10/2009 | Poulin | .................... | G16H 50/70 |

| | | | | |
|---|---|---|---|---|
| 2016/0292456 A1 * | 10/2016 | Dubey | .................. | G06F 21/602 |
| 2018/0052960 A1 * | 2/2018 | Hamilton | ............... | G06Q 10/10 |
| 2018/0342323 A1 * | 11/2018 | Shankar | ................. | G16H 10/60 |
| 2019/0034589 A1 * | 1/2019 | Chen | ....................... | G06N 3/045 |
| 2021/0248268 A1 * | 8/2021 | Ardhanari | .............. | G06N 20/00 |
| 2021/0319861 A1 * | 10/2021 | Mullenbach | ........... | G16H 70/20 |

(Continued)

OTHER PUBLICATIONS

Xiang Y, Xu J, Si Y, Li Z, Rasmy L, Zhou Y, Tiryaki F, Li F, Zhang Y, Wu Y, Jiang X, Zheng WJ, Zhi D, Tao C, Xu H. Time-sensitive clinical concept embeddings learned from large electronic health records. BMC Med Inform Decis Mak. Apr. 9, 2019;19(Suppl 2):58. doi: 10.1186/s12911-019-0766-3. (Year: 2019).*

(Continued)

*Primary Examiner* — Sun M Li
(74) *Attorney, Agent, or Firm* — SMITH GAMBRELL & RUSSELL LLP

(57) ABSTRACT

A method and system for merging healthcare records across multiple locations is presented. The method first creates anonymized healthcare records by removing personally identifiable information. The method then converts each record into an embedding and appends a site locator identifying only the originator of the healthcare record. Then these embeddings are combined with similarly processed embeddings from multiple sites to create a merged database of embeddings derived from patient healthcare records. A classifier is trained to predict likely outcomes based on the merged database of embeddings. For a new patient, the corresponding healthcare record is converted to an embedding and the merged database of embeddings is then searched for a most similar patient and a treatment is recommended for the new patient, based on the prediction of the classifier.

21 Claims, 24 Drawing Sheets

(56) References Cited

U.S. PATENT DOCUMENTS

| | | | |
|---|---|---|---|
| 2022/0059228 A1* | 2/2022 | Chen | G06F 16/254 |
| 2022/0180982 A1* | 6/2022 | Todd | G16H 10/60 |
| 2023/0010686 A1* | 1/2023 | Lesh | G16H 50/70 |
| 2024/0119176 A1* | 4/2024 | Ardhanari | G06N 3/047 |

OTHER PUBLICATIONS

Wavelet-Based ECG Steganography for Protecting Patient Confidential Information in Point-of-Care Systems, by Ayman Ibaida and Ibrahim Khalil, IEEE Transactions on Biomedical Engineering, vol. 60, No. 12, Dec. 2013 (Year: 2013).*

Measuring Patient Similarities via a Deep Architecture with Medical Concept Embedding, by Zihao Zhu , Changchang Yin , Buyue Qian , Yu Cheng† , Jishang Wei‡ , Fei Wang, arXiv:1902.03376v1 [stat.ML] Feb. 9, 2019. (Year: 2019).*

Wu T, Wang Y, Wang Y, Zhao E, Yuan Y. Leveraging graph-based hierarchical medical entity embedding for healthcare applications. Sci Rep. Mar. 12, 2021;11(1):5858. doi: 10.1038/s41598-021-85255-w. PMID: 33712670; PMCID: PMC7955058. (Year: 2021).*

Xiang Y, Xu J, Si Y, Li Z, Rasmy L, Zhou Y, Tiryaki F, Li F, Zhang Y, Wu Y, Jiang X, Zheng WJ, Zhi D, Tao C, Xu H. Time-sensitive clinical concept embeddings learned from large electronic health records. BMC Med Inform Decis Mak. Apr. 9, 2019;19(Suppl 2):58. doi: 10.1186/s12911-019-0766-3.PMID: 30961579 (Year: 2019).*

* cited by examiner

1500

1502
BUILD AND TRAIN CLASSIFIER ∀ DISEASE TYPE

1504
PREDICT DISEASE TYPE

1506
RECEIVE INCOMING PATIENT WITH DIAGNOSIS

1508
CONCATENATE DIAGNOSIS & EXPECTED TREATMENT

1510
CREATE PATIENT GRAPH *g*

1512
CALCULATE TYPES OF KERNEL FEATURE VECTOR

1514
GET PROBABILITY OUTPUT w/ DISEASE DIAGNOSIS TYPE

1516
SELECT AND PRESCRIBE LIKELY EFFECTIVE TREATMENT

1900

SYSTEM FOR PROVIDING VALIDATION OF DEEP LEARNING BASED PRESCRIPTION EFFICACY

BACKGROUND OF THE INVENTION

The present invention relates to systems and methods that merge patient medical information for predicting the success or failure of a treatment using accurate and efficient models to predict the potential success of a specific treatment for a given ailment. The present invention further relates to systems and methods for analyzing electronic health records of many patients, without loss of privacy or without exposing the patients' information to an unauthorized third party.

In healthcare systems which do not have large databases of patient information available for analysis, there is a problem with discovering which treatments or medications might work best with any given patient, by, for instance, identifying similar patients with the similar conditions who have been successfully treated in the past. Healthcare systems with distributed stores of information which are not integrated across multiple providers face the additional problem of how to access a large enough store of patient medical information to provide worthwhile recommendations while also not sharing any personal information.

Accordingly, a need arises for systems and methods that predict the success or failure of a treatment for a disease or for a condition by more effectively using information in health records of previous treatments. A further need arises for systems and methods that provide a means for analyzing and discovering information in electronic health records across multiple healthcare institutions without exposing the personal information within the records to other people.

SUMMARY OF THE INVENTION

Aspects of the disclosure relate to systems and methods for merging healthcare records across multiple sites while maintaining the patients' rights to privacy and also providing explanations as to why a treatment is recommended for a particular patient. Merging databases of patient healthcare records enables the analysis of a larger, more diverse data set to better identify previous healthcare records most similar to a present patient's healthcare record and to then recommend a treatment most likely to succeed for the present patient.

This disclosure describes a system for computing a probable treatment efficacy, for use with a user device. The system comprises a processor and memory accessible by the processor. The memory stores computer program instructions which are executable by the processor to perform steps. A first step is creating a first plurality of embeddings from a first plurality of patient healthcare records having had personally identifiable information removed and having added a first site locator, associated with a first site, to each embedding of the first plurality of embeddings. A second step is creating a second plurality of embeddings from a second plurality of patient healthcare records having had personally identifiable information removed and having added a second site locator, associated with a second site, to each embedding of the second plurality of embeddings. The system then combines the first plurality of embeddings and the second plurality of embeddings into a merged database of embeddings. The system receives a new patient healthcare record for a new patient and creates a new embedding from the new patient healthcare record. The system then calculates a probable efficacy of a selected treatment of a plurality of treatments based on the merged database of embeddings. Based on the new embedding and the calculated probable efficacy, the system determines a recommended treatment, of the plurality of treatments, to be prescribed to the new patient and reports the recommended treatment to the user device.

In an embodiment, the first plurality of healthcare records may be a copy of an original first plurality of healthcare records at the first site and the second plurality of healthcare records may be a copy of an original second plurality of healthcare records at the second site. In an embodiment, after the creation of the first plurality of embeddings, the first plurality of healthcare records is deleted. In an embodiment, after the creation of the second plurality of embeddings, the second plurality of healthcare records is deleted. In an embodiment, calculating the probable efficacy of the selected treatment of the plurality of treatments based on the merged database of embeddings, performed by the processor, may comprise capturing a plurality of features from each embedding of the merged database of embeddings and training a classification model using a subset of the captured plurality of features of each embedding of the merged database of embeddings to predict the probable efficacy of the selected treatment. In an embodiment, the subset of the captured plurality of features is based on demographic information. In an embodiment, the demographic information comprises at least one of geographical data, racial data, ethnic data, cultural data, gender-related data, or age-related data.

In an embodiment, the system may also perform additional steps. For example, the processor may receive a site locator of an embedding of the merged database of embeddings most closely associated with the recommended treatment. The processor may request additional information about the recommended treatment from a selected site identified by the selected site locator. The processor may receive the requested additional information from the selected site and report to the user device the received additional information along with the recommended treatment. In an embodiment, the system may also receive from the user device an acknowledgement when the recommended treatment was administered to the new patient and may also receive an indication of the efficacy of the recommended treatment. In an embodiment, the system may further comprise an accelerator coupled to the processor to assist in calculating the probable efficacy and determining the recommended treatment. In an embodiment, the system may further comprise an accelerator coupled to the processor to assist in capturing the plurality of features and training the classification model to predict the probable efficacy of the selected treatment. In an embodiment, the accelerator comprises one or more additional processors configured to function as a single core to assist the processor.

In an embodiment, a compute platform may calculate a probable treatment efficacy by creating a semantic map from a merged database of embeddings, wherein each embedding of the merged database of embeddings is associated with a site, a site locator, and a treatment of a plurality of treatments. The compute platform comprises a processor and memory accessible by the processor, wherein computer program instructions are stored in the memory and executable by the processor to perform multiple steps. A first step is receiving a new embedding of a new patient's healthcare records from a new site. The compute platform may determine a recommended treatment from the plurality of treatments to be recommended to the new patient by identifying a previous embedding of the merged database of embeddings similar to the new embedding. The compute platform reports to the new site the recommended treatment of the plurality of treatments and the site locator associated with the previous embedding. The compute platform links the new site to a site associated with the previous embedding based on the site locator associated with the previous embedding and requests that the site associated with the previous embedding provide additional information to the new site to substantiate that the recommended treatment is applicable to the new patient.

In an embodiment, the compute platform identifies the previous embedding of the merged database of embeddings by calculating a similarity of a plurality of similarities between the new embedding and each embedding of the merged database of embeddings and identifying the previous embedding as that embedding of the merged database of embeddings which has the greatest similarity of the plurality of similarities, and wherein if no similarity of the plurality of similarities exceeds a pre-defined threshold, then not identifying a previous embedding and reporting the lack of a previous embedding to the new site.

In an embodiment, the compute platform identifies the previous embedding of the new embedding by capturing a plurality of features from each embedding of the merged database of embeddings. The compute platform then trains a classification model using a subset of the captured plurality of features of each embedding of the merged database of embeddings. The compute platform then applies the trained classification model on the new embedding to determine a probability that each treatment of the plurality of treatments will be effective for the new patient. Then the compute platform identifies as the previous embedding of the merged database of embeddings that embedding of the merged database of embeddings which is associated with the highest probability that the associated treatment will be effective for the new patient. In an embodiment, the compute platform further comprises an accelerator coupled to the processor to assist in determining the recommended treatment from the plurality of treatments. In an embodiment, the compute platform further comprises an accelerator coupled to the processor to assist in capturing the plurality of features and in training the classification model.

In an embodiment, a system is described for use with a user device, for computing a probable treatment efficacy on a merged database of embeddings, wherein each embedding of the merged database of embeddings is associated with a site, a site locator, and a treatment of a plurality of treatments. The system comprises a processor and memory accessible by the processor, wherein computer program instructions are stored in the memory and executable by the processor. The system performs several steps. The system captures a plurality of features from each embedding of the merged database of embeddings. The system then trains a classification model using a subset of the captured plurality of features of each embedding of the merged database of embeddings to return a probable efficacy of a treatment of the plurality of treatments and sends the trained classification model to the user device. The user device receives a new embedding associated with a new patient's healthcare records from a new site. The user device determines a recommended treatment of the plurality of treatments, to be prescribed to the new patient based on the trained classification model and the new embedding. The user device also determines a recommended site associated with the recommended treatment of the plurality of treatments. The user device then establishes a connection to the recommended site to retrieve validation information to support the recommended treatment.

In an embodiment, receiving a new embedding at the user device comprises multiple steps. The user device receives a copy of the new patient's healthcare records from the new site and creates the new embedding based on the copy of the new patient's healthcare records after which the user device deletes the received copy of the new patient's healthcare records, leaving only the embedding. In an embodiment, the system further comprises an accelerator coupled to the processor for assisting in capturing the plurality of features and in training the classification model to determine the probable efficacy of the treatment of the plurality of treatments.

A system is described for creating a merged database of embeddings of patient healthcare records for use with a user device. The system comprises a processor and memory accessible by the processor, wherein computer program instructions are stored in the memory and executable by the processor to perform certain steps. A first step is removing personally identifiable information from each patient healthcare record of a first plurality of patient healthcare records from a first site. A second step is removing personally identifiable information from each patient healthcare record of a second plurality of patient healthcare records from a second site. The system then creates a first plurality of embeddings from the first plurality of patient healthcare records and adds a first site locator, associated with the first site, to each embedding of the first plurality of embeddings. The system then creates a second plurality of embeddings from the second plurality of patient healthcare records and adds a second site locator, associated with the second site, to each embedding of the second plurality of embeddings. The system then combines the first plurality of embeddings and the second plurality of embeddings into a merged database of embeddings. The system then captures a plurality of features from each embedding of the merged database of embeddings. The system then trains a classification model using a subset of the captured plurality of features of each embedding of the merged database of embeddings to determine the probable efficacy of each treatment of the plurality of treatments and transmits the trained classification model to the user device.

In an embodiment, the first plurality of healthcare records is a copy of an original first plurality of healthcare records from the first site, and the second plurality of healthcare records is a copy of an original second plurality of healthcare records from the second site. In an embodiment, the user device performs additional steps. The user device receives the trained classification model and also receives a new patient healthcare record. The user device converts the new patient healthcare record into a new embedding. The user device determines a recommended treatment of the plurality of treatments to be prescribed to the new patient based on the trained classification model and the new embedding. The user device determines a recommended site associated with the recommended treatment of the plurality of treatments. The user device establishes a connection to the recommended site to retrieve validation information in support of the recommended treatment. The user device displays the recommended treatment and the validation information in support of the recommended treatment. In an embodiment, the system transmits from the user device to the processor, an acknowledgement when the recommended treatment was administered to the new patient. In an embodiment, the system transmits from the user device to the processor, an indication of the efficacy of the recommended treatment. In an embodiment, the system further comprises an accelerator coupled to the processor for assisting in capturing the plurality of features and in training the classification model to determine the probable efficacy of each treatment of the plurality of treatments.

BRIEF DESCRIPTION OF THE DRAWINGS

A more particular description of the invention, briefly summarized above, is had by reference to embodiments, some of which are illustrated in the appended drawings. It is to be noted, however, that the appended drawings illustrate only typical embodiments of this invention and the invention may admit to other equally effective embodiments.

Figure 1:
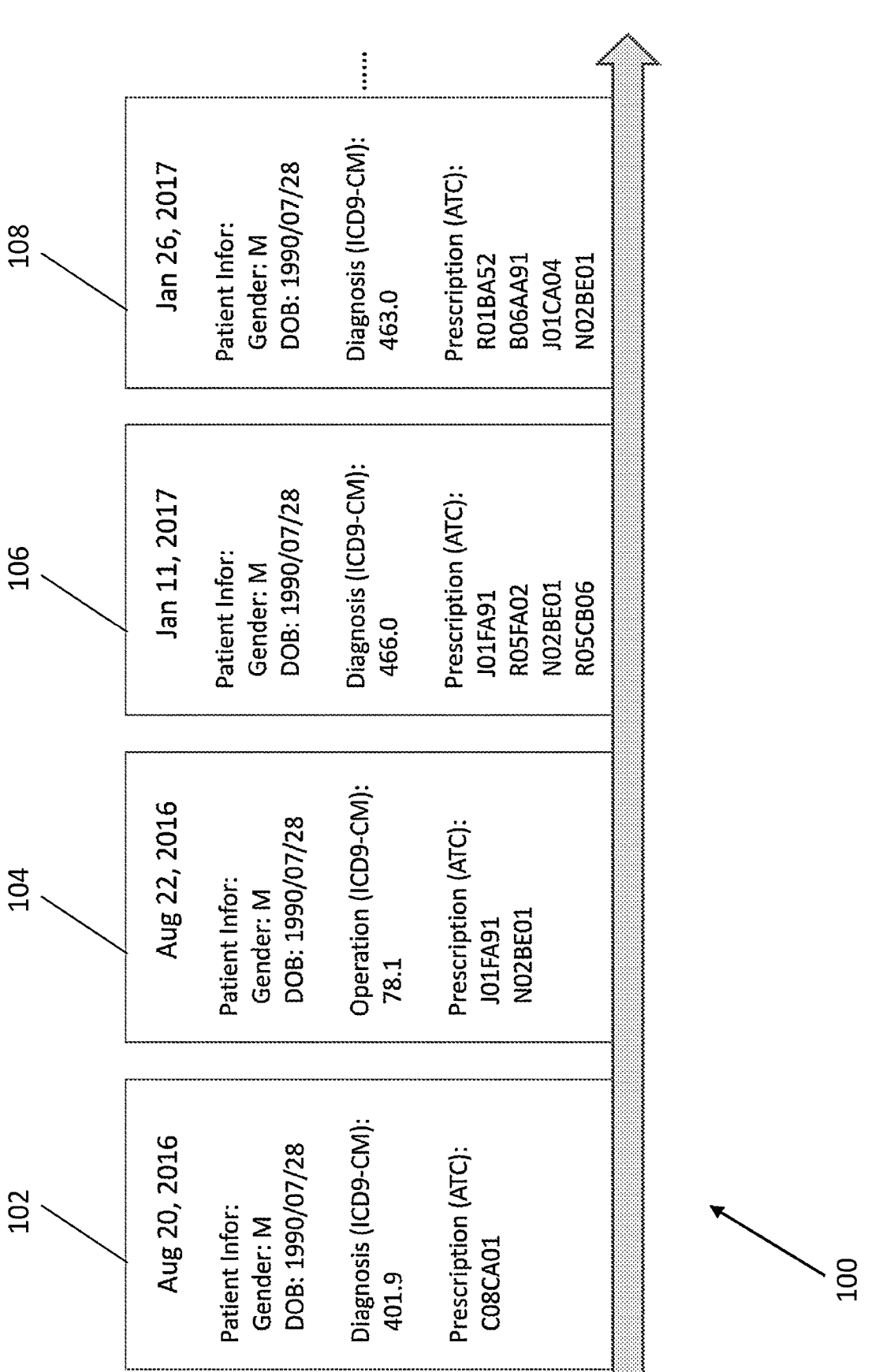
FIG. 1 is an exemplary illustration of a set of patient healthcare records, according to embodiments of the present systems and methods.

Other features of the present embodiments will be apparent from the Detailed Description that follows.

DETAILED DESCRIPTION

In the following detailed description of the preferred embodiments, reference is made to the accompanying drawings, which form a part hereof, and within which are shown by way of illustration specific embodiments by which the invention is practiced. It is to be understood that other embodiments may be utilized and structural changes may be made without departing from the scope of the invention. Electrical, mechanical, logical, and structural changes may be made to the embodiments without departing from the spirit and scope of the present teachings. The following detailed description is therefore not to be taken in a limiting sense, and the scope of the present disclosure is defined by the appended claims and their equivalents.

A healthcare system contains many fragmented sources of information about many patients. For instance, within the United States, different hospitals within the same system can find it difficult to share the healthcare records information with each other, even when it relates to the same patient. Regulatory issues (such as HIPAA) and patient privacy rights can require that healthcare providers not share personally identifiable information (PII), or that the healthcare providers may not want to provide such healthcare records immediately without an internal review. To maintain patient privacy methods and systems are disclosed herein to merge, from a plurality of healthcare databases, the embeddings of an analysis on each healthcare database while removing any information that identifies patients.

As used herein, an 'embedding' of a patient healthcare record is defined as a vector data structure that is created from a patient's healthcare record which comprises important information from the patient healthcare record along with a site locator. The site locator identifies only from which location or database the patient healthcare record originates, but no other personally identifiable information (PII). The embeddings lack personally identifiable information about each patient, but retain the information required to compare with other potentially similar patients in any of the databases so linked.

If required, the system and method may point to the similar patient embedding.

In some embodiments, should the medical staff require additional information (e.g., more clinically relevant data), to explain their recommendations for the treatment of the current patient, they may contact the originator of that particular patient record. In some embodiments, the system automatically requests such additional information from the data originator. In this manner, the method and system provide explanations when the medical staff require additional explanation before recommending a particular treatment, approach, therapy, or medicine for a new patient.

The methods and systems for finding previous similar medical records follow those of U.S. Pat. Nos. 11,238,966 and 11,410,763 which are incorporated herein in their entirety by reference.

At each local site of stored healthcare records, some of the embodiments disclosed herein create (dense) vectors of patient records. Since the vectors are not patient specific, rather they are learned patient groupings, no personally identifiable information (PII) is associated with any vector. After these vectors are created, they are tagged with a site key or site ID or site locator which indicates the location of the original database where the health record was located. In an embodiment, the site keys are encrypted.

The localized, learned, vectors are distributed across sites (to all or a subset of sites) replicating part, or all, of the data across the sites or are sent to one or more centralized site(s). The database of healthcare records, now as learned vectors (i.e., embeddings) is merged and shared. The merging of these databases may be based on geographic boundaries, population demographics, diagnostics, medical conditions, medical departments, or other categories of the generating sites, or based on other rules, including temporal or seasonally based, to obtain the best coverage to find the most similar medical to the current patient's healthcare record so that an optimal treatment may be recommended.

Vectors from selected sites are merged and are (deeply) learned or simply joined, while maintaining their source identifier, the site locator or site identifier/site ID.

In some embodiments, the interpretability of the efficacy prediction is enabled at the central site. However, explanations must be requested, which requires communication with the identified site. The identifier of the original source vector is routed to the original local site for justification of the result in the explanation. In some cases, the provided explanations might require the removal of PII from any patient healthcare record.

In the United States, for example, every healthcare system is a separate system. Hospitals do not share data because they have no incentive to do so and are, indeed, afraid to do so due to HIPAA requirements, for example. In the United States, many healthcare systems do not share data, even within the same system. Alternatively, different health systems have different databases of electronic healthcare records, which makes direct sharing of healthcare records difficult from a technical perspective, not taking into account issues of patient privacy.

In an embodiment, the process comprises the following steps:
1) Create a temporary copy of each patient's electronic health record from one site.

2) Remove any personally identifiable information (PII) from each temporary copy of the electronic healthcare record.
3) Append a site locator to the temporary copy (optional).
4) Create an embedding (i.e., a vector) based on each temporary copy of the healthcare record with the appended site locator.
4b) Append site locator (if not done at step 3)
5) Delete all the temporary copies of the healthcare records.
6) Distribute the site-id tagged embeddings across multiple sites to create a merged database.
7) Apply the above-referenced US patents to the embeddings in the merged database.
8) Receive, from the site of the previous medical record most similar to the current patient's medical record, an indication of efficacy of the recommended treatment from the requesting patient site once efficacy is determined (optional).

This method can vary the order of the steps. For instance, the embedding may be created after the PII has been removed from a temporary record derived from the patient health record, and then the site locator is added to the embedding. In other embodiments, the patient health records are annotated with the site locator of where and when that record was created. In yet other embodiments, the site locator is added to existing records and embeddings in a batch process. Since the information is combined anonymously across multiple sites by sharing the embeddings and not the original data, the patients' privacy rights are protected, while also enhancing the possibility of finding a more similar record to the current patient's healthcare record. This method and system also provide explanations to the present patient's medical advisor-why is the found embedding most similar to the embedding of the current patient's healthcare record? Why is the treatment regime followed by a previous patient likely to be the treatment most likely to benefit the current patient? If the medical advisor wishes to confirm, then the medical advisor contacts the originator of that particular embedding to request additional information. Since this additional information might include PII, there must be an evaluation of such a request by the healthcare provider to protect their patient's privacy.

In an embodiment, this method and system provide, optionally if so desired, an indication of the efficacy of the recommended treatment, once such efficacy is determined, which is sent to the previous patient's site from the requesting patient's site. The most similar previous patient's site can record the potential efficacy of the recommended treatment for the given ailment in a corresponding addendum associated with the medical record of the previous patient. The indication may be sent automatically once efficacy is determined or sent in response to a request from the new patient's site.

The site locator or site ID of the owner of any healthcare records can be one or more of the following items: the name of the hospital or healthcare provider, the GPS coordinates of the healthcare records keeper's primary address, a postal address or a physical address of the records keeper's address, a phone number associated with the healthcare records keeper, the employer identification number, an email address or an IP address of the healthcare records keeper, a randomly (or non-randomly) assigned number by the system for each site as it becomes necessary to distinguish locations. Any unique identifier suffices as the site locator so long as the user of the embeddings can request from that site additional details. Other examples of unique identifiers are known to those skilled in the art in addition to those examples cited here.

The site locator identifies the custodian of the patient health records. Over time, the custodian may change. For example, hospitals may close, consolidations of health systems may occur, the records may be held by an archival site, etc. Accordingly, the site locator can change over time to maintain traceability of individual patient health records.

Under certain circumstances, it is necessary to ask the originator to supply at least some of the deemed similar patient's records to substantiate the treatment recommendation of a new patient, and that healthcare system can decide, perhaps on a case-by-case basis, whether or not to provide the requested data. The embeddings are useful here since they can be shared without violating regulatory/privacy concerns. In an embodiment, such a request is initiated once the most similar patient record has been identified, by an automated request to the location where the records of the most similar patient are stored. In an embodiment, the holder of these patient health records can have their own rules or policies regarding which portion of a patient health record to share.

In an example, a first hospital may receive a new patient with a complaint and identify a similar previous complaint and treatment. The first hospital may then request confirmation from a second hospital that the previous patient (i.e., the most similar patient to the new patient) followed a particular treatment regimen. In another example, the first hospital's system may request from the second hospital more details about the previous patient, such as which other treatments may have been tried in the past for the deemed similar patient for the same ailment. Thus, the first hospital may request such additional information to enable the first hospital's staff to provide the best recommendation to their current patient.

It is to be understood that the term "first hospital" is merely an example and can be broadly construed to include any doctor's office, medical clinic, ambulance or any other location where a patient receives treatment for a medical condition from a medical provider. Further, it is to be understood that the term "new patient" means a current patient seeking medical care for a medical condition from a medical provider. The term "new patient" does not necessarily exclude a patient who may have received treatment in the past from the medical provider and who has a patient healthcare record included in the merged database for the same medical condition or for a different medical condition.

In an example, a patient at a first hospital has a urinary tract infection (UTI). The method is applied to a database of embeddings of patient records from at least one other hospital (and likely from many other hospitals). A similar embedding is found from the (merged) database of embeddings. The deemed similar patient was prescribed a particular medication for a UTI, which proved very effective. The first hospital may request confirmation from the second hospital of other treatments which the deemed similar patient had received in the two months prior to the treatment for the urinary tract infection. The first hospital also shares the embedding which most closely matches the embedding of the patient's healthcare record. The second hospital has in place rules to share, for example, only the past three months of a patient's health records. The second hospital can verify the deemed similar patient from the embedding identified by the first hospital as the closest match for the patient. If necessary, the second hospital can compare and match the precise record of the provided embedding with the embeddings of their own patient health records. In this example, the second hospital provides the requested additional two months of treatment options to the first hospital.

Embodiments of the present systems and methods may provide techniques to predict the success or failure of a drug or treatment using an accurate and efficient model to predict the success potential of a specific drug prescription or of a specific treatment for a given ailment. For example, embodiments may predict success or failure of a drug prescription or treatment by formulating a binary graph classification problem without the need of electronic phenotyping. First, training data are identified, such as success and failure patients for target disease treatment within a user-defined time period. The set of medical events from patient healthcare records that occur within this time quantum is extracted. Then, a classification task is performed on the graphical representation of the patient healthcare records. The graphical representation provides an opportunity to model the patient healthcare records in a compact structure with high interpretability.

Embodiments of the present systems and methods may provide a kernel-based deep architecture to predict the success or failure for drug prescription or for treatment given to a patient. The success and failure of the medication or the treatment on patients are identified for targeted evaluation to define the success and failure cases. A patient healthcare record prior to the disease diagnosis is included for each patient, and their graphical representation (e.g., patient graph) is built, where nodes denote all medical events with day differences as edge weights. The binary graph classification task is performed directly on the patient graph via a deep architecture. Interpretability is readily available and easily accepted by users without further post-processing due to the nature of the graph structure.

Embodiments of the present systems and methods may provide a novel graph kernel, the temporal proximity kernel, which efficiently calculates temporal similarity between two patient graphs. The kernel function is proven to be positive definite, increasing the model availability by using a kernelized classifier such as Support Vector Machine (SVM). To obtain the multi-view aspect, the temporal proximity kernel is combined with the node kernel and with the shortest path kernel as a single kernel through multiple kernel learning.

To perform large scale and noise-resistant learning objectives, embodiments may transfer the original task to similarity-based classification, where each row in the kernel gram matrix is considered as a feature vector with each dimension expressing the similarity measurement with specific training examples. A multiple graph kernel fusion approach is proposed to learn kernel representation in an end-to-end manner for the best kernel combination. Representation learning is a typical kernel approximation which preserves the similarity while reducing the dimension for the original kernel matrix. The embedding weight for each kernel supports the interpretation to the prediction via most similar cases by selecting top relevant embedding dimension.

Embodiments of the present systems and methods may provide a cross-global attention graph kernel network to learn optimal graph kernels on a graphical representation of patient healthcare records. The novel cross-global attention node matching automatically captures relevant information in biased long-term disease progression. In contrast to attention-based graph similarity learning that relies on a pairwise comparisons of training pairs or triplets, this matching is performed on a batch of graphs simultaneously by a global cluster membership assignment. This is accomplished without the need to generate training pairs or triplets for pairwise computations and seamlessly combines classification loss. The learning process is guided by cosine distance. The resulting kernel, compared to its Euclidean distance counterpart, has better noise resistance under a high dimension space. Unlike distance metric learning and the aforementioned graph similarity learning, the learned distance and graph kernel are aligned to a classification objective. An end-to-end training is formulated by jointly optimizing contrastive and kernel alignment loss with a Support Vector Machine (SVM) primal objective. Such a training procedure encourages node matching and similarity measurement to produce ideal classification, providing interpretation on prediction. The resulting kernel function can be directly used by an off-the-shelf kernelized classifier (e.g., scikit-learn SVC). The cross-global attention node matching and kernel-based classification makes it interpretable in both knowledge discovery and prediction case study.

In embodiments, up to three kernels are used to achieve multi-view similarity measurement-reducing potential healthcare record "noise". For example, some training examples may dominate prediction results due to higher kernel value. Embodiments may incorporate additional kernels to balance this effect to improve prediction. Example of kernels that may be used include a Temporal Proximity Kernel, which may provide temporal ordering and time difference of medical events, a Shortest Path Kernel, which may provide general connectivity of medical events, and a Node Kernel, which may provide general overlapping of medical events.

Embodiments may provide one-shot disease processing, for example, for an antibiotic medication. To perform one-shot disease processing, a database of medical history data is partitioned according to disease diagnosis. A suggested medication is attached to the data and used to predict a likelihood of success or failure of the medication and to identify similar individuals.

Embodiments may provide COVID-19 processing based on a presumptive medication. A database of medical history data is partitioned according to those having used the presumptive medication. Patient graphs are retained up until the last presumptive medication use within a surveillance window. A suggested medication is attached to the data and used to identify similar individuals indicating a likelihood of success or failure of use of the suggested medication for others diseases under consideration.

An exemplary set of patient healthcare records 100 is shown in FIG. 1. patient healthcare records 100 may include a plurality of records 102-108. Typically, each record relates to a different patient interaction with medical staff, diagnosis, test result, etc., and may include information such as the date of the interaction, diagnosis, test result, etc., demographic information about the patient, such as identity, gender, date of birth, ethnic background, information about the diagnosis or diagnoses, information about the prescription(s) or treatment(s), etc.

Figure 2:
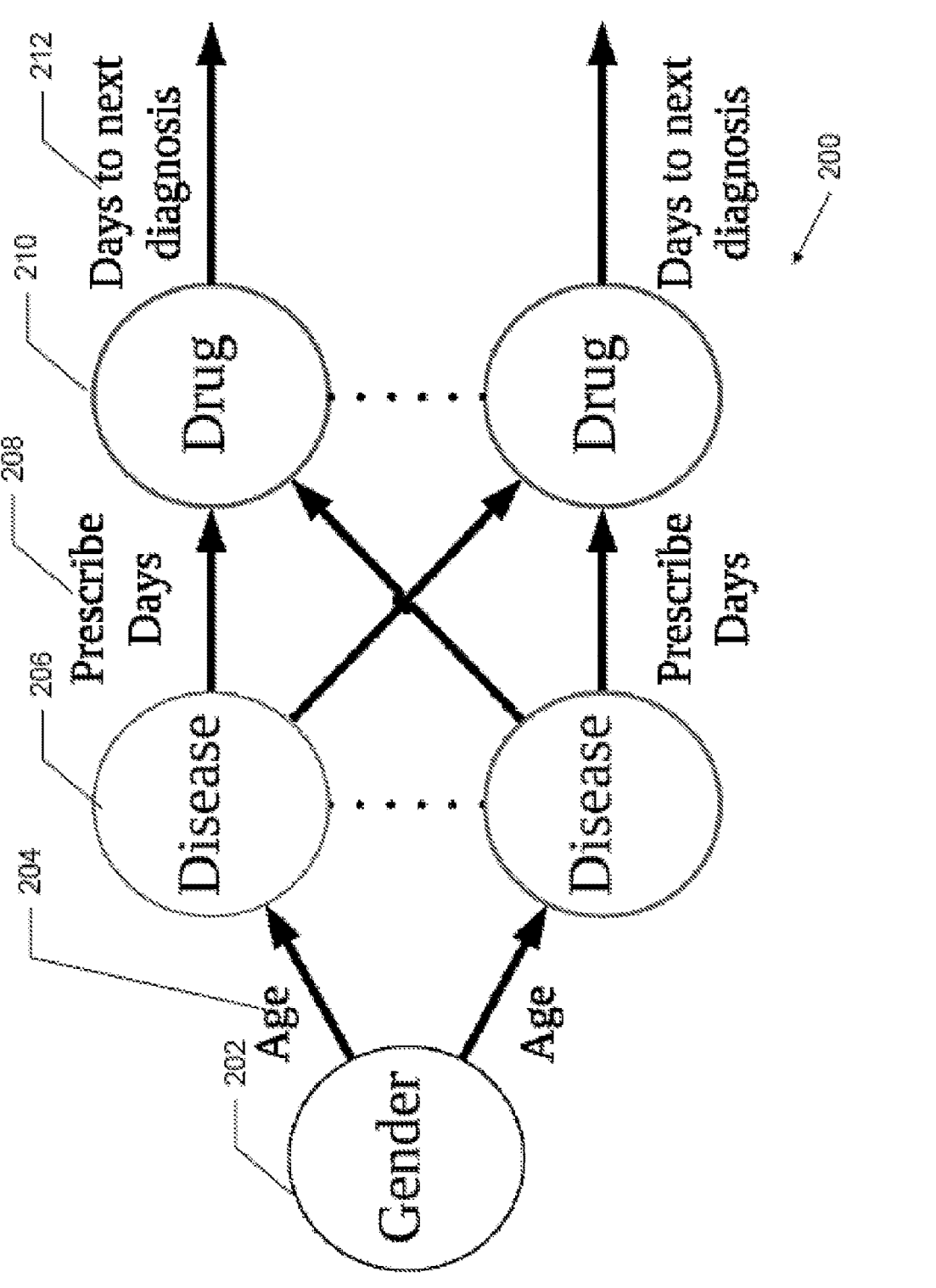
FIG. 2 is an exemplary illustration of a Directed Acyclic Graph (DAG), according to embodiments of the present systems and methods.

A patient's patient healthcare record is formulated as a Directed Acyclic Graph (DAG) 200, an example of which is shown in FIG. 2. For example, each node represents a medical event, such as a disease diagnosis 206, a drug prescription or treatment 210, etc., and an edge between two nodes represents an ordering with the time difference as edge weight (e.g., days). For example, the edge weights may include the prescription or treatment day 208, the days to next diagnosis 212, etc. The demographic information of the patient, such as, gender, may be represented as a node 202 that connects to the first medical event 206 with age 204 as an edge weight. In this example, only gender and age are used as demographic information to simplify the model, but other information could also be incorporated such as a patient's ethnic background or geographical data such as where a patient was born or lived.

Figure 3:
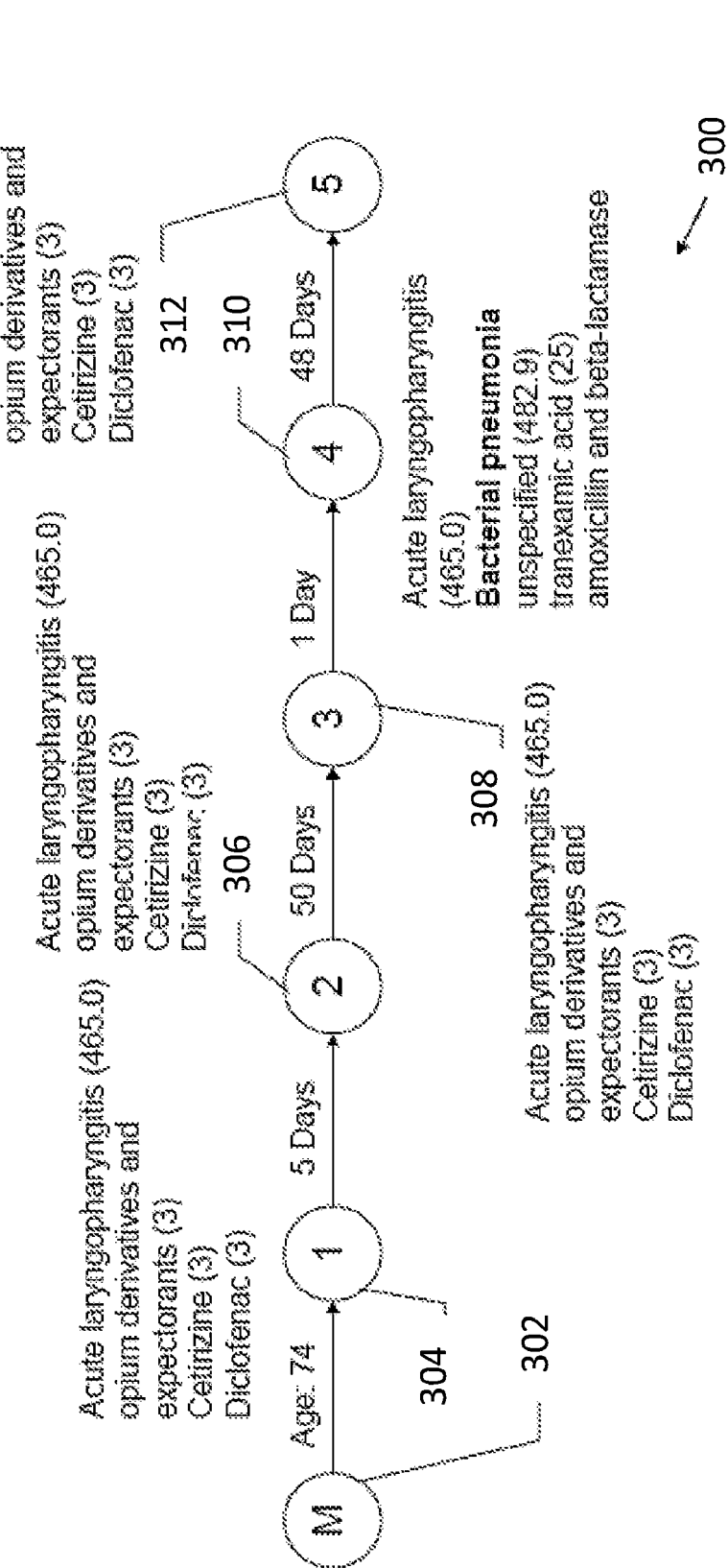
FIG. 3 is an exemplary illustration of a patient DAG illustrating success with a proposed pneumonia treatment, according to embodiments of the present systems and methods.

An example 300 of a patient DAG illustrating success with pneumonia treatment is shown in FIG. 3. In this example, the diagnosis at each stage 304-312 of treatment, as well as the prescriptions/treatments at each stage of treatment are shown. This example illustrates a success because there is no diagnosis of pneumonia for more than four weeks after the end of the course of treatment, stage 5 312.

Figure 4:
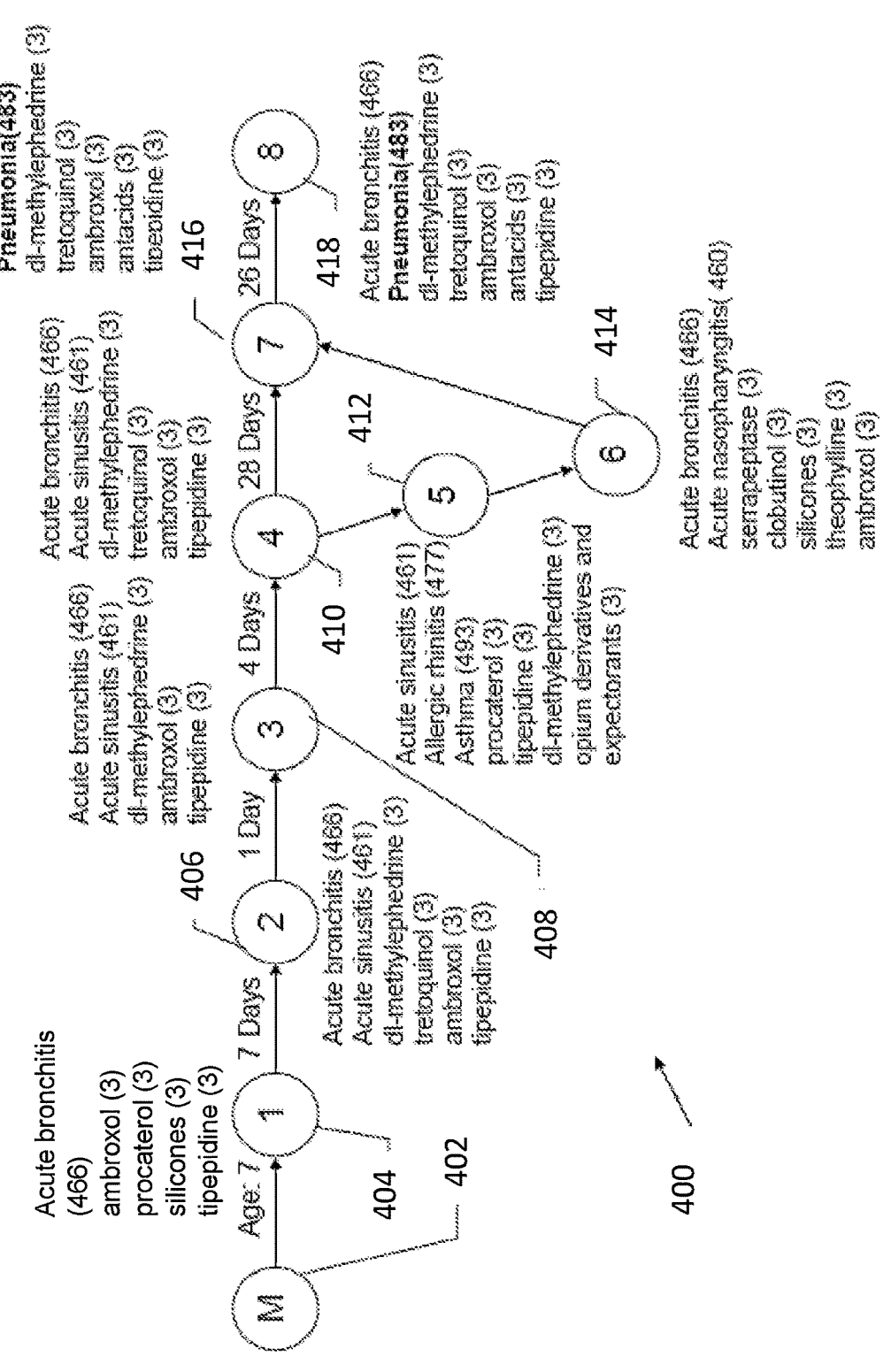
FIG. 4 is an exemplary illustration of a patient DAG illustrating failure with a proposed pneumonia treatment, according to embodiments of the present systems and methods.

A more detailed example 400 of a patient DAG illustrating failure with pneumonia treatment is shown in FIG. 4. In this example, the diagnosis at each stage 404-418 of treatment, as well as the prescriptions/treatments at each stage of treatment are shown. This example illustrates a failure in treatment of pneumonia 416 because there is a diagnosis of pneumonia within four weeks after a stage of treatment at stage 8 418.

In embodiments, an patient healthcare record graph representation is defined as follows: Given n medical events, set $M=\{(m_1, t_1), \ldots, (m_n, t_1)\}$ represents a patient's patient healthcare records with $m_i$ denoting a medical event such as diagnosis, and $t_i$ denoting the time for $m_i$. Then the patient graph is defined as follows: Definition 1 (Patient Graph). The patient graph $P_g=(V,E)$ of events M is a weighted directed acyclic graph with its vertices V containing all events $m_i \in M$ and edges E containing all pairs of consecutive events $(m_i, m_j)$. The edge weight from node i to node j is defined as $W_{ij}=t_j-t_i$, which defines the time interval between $m_i, m_j$.

Figure 5:
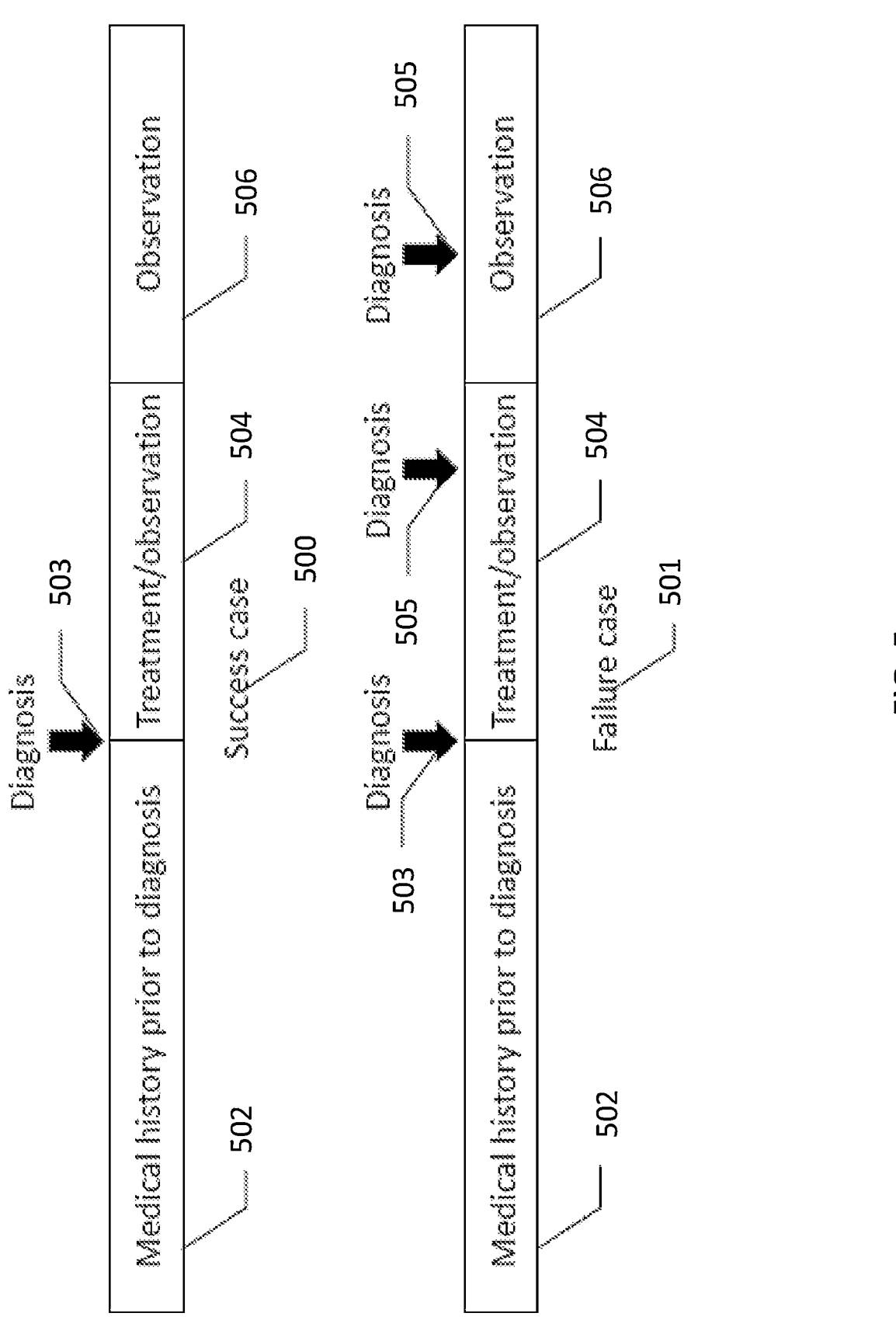
FIG. 5 is an exemplary illustration of examples of success and failure cases, according to embodiments of the present systems and methods.

Given a disease diagnosis of a patient, a drug prescription or treatment for the diagnosis is considered a failure if the patient has a second same diagnosis within an observation window. Otherwise, the prescription or treatment is considered a success. Examples of success 500 and failure 501 cases are shown in FIG. 5. The failure case 501 is labelled as positive, and the success 500 case is labelled as negative. To capture historical factors, each case may contain previous medical history events 502 prior to the diagnosis date 503 in a user-defined period. Each case is treated as a subset of patient healthcare records as shown in FIG. 1, which contains a multiple-event single-patient healthcare record. In short, each case contains the medical events before and after the disease diagnosis for a user-defined period. A drug prescription or treatment for the diagnosis is considered a failure if the patient has a second same diagnosis 505 within an observation window, which may include a period of treatment and observation 504, and a period of observation 506.

In embodiments, this is extended to define the success or failure of treatment plan for a chronic disease, following the guidelines published by the National Medical Association for selected chronic diseases. Generally, an observation window 506 is defined after a treatment period 504 (which may include observation as well) to monitor whether the given treatment plan achieves its treatment objective (such as no severe complication occurrence in 5 years). Given a chronic disease diagnosis, a treatment is considered a failure if the patient is diagnosed 505 with a selected severe complication or comorbidity within the post treatment observation window 506. Otherwise, the treatment is considered a success. Due to the chronic disease long-term progression where past factors are potentially decisive, all medical histories are included prior to the first diagnosis date. Each case is treated as a set of healthcare records from a patient's patient healthcare record as in FIG. 1. The terms patient and case is used interchangeably herein.

Given a patient healthcare record, the patient's current diagnosis, and the drug prescription or treatment to the current diagnosis, embodiments may predict the success or failure of a prescribed medication or treatment. A temporal graph $G_i$ is created that consists of the current diagnosis, the drug prescription or treatment to the current diagnosis, and the medical events in the patient healthcare record prior to the current diagnosis. Then a binary graph classification problem is formulated on the resulting temporal graph by considering the following dual optimization problem for a Support Vector Machine (SVM):

$$\text{maximize}_{\alpha} \sum_i \alpha_i - \frac{1}{2} \sum_{j,k} \alpha_i \alpha_k y_i y_k K(G_j, G_k) \tag{1a}$$

$$\text{subject to } 0 \le \alpha_i \le C, i = 1, \dots, N \tag{1b}$$

$$\sum_i \alpha_i y_i = 0, i = 1, \dots, N \tag{1c}$$

where K is a positive definite graph kernel on input graphs $G_j$, $G_k$. C is a regularization parameter, and b is a bias term. Given the graph $G_i$, the bias term b can be computed by $$b = y_i - \sum_{j=1} \alpha_j y_j K(G_i, G_j) \tag{2}$$

and the decision function is defined as:

$$f(G) = \sum_{i=1}^{N} \alpha_i y_i K(G_i, G) + b \tag{3}$$

Embodiments may perform a binary graph classification on graph patient healthcare record. Given success and failure cases with their associated label $(g_i, y_i)$, a classifier should learn such that $f(g_i)=y_i$ where $y_i \in \{0, 1\}$ to predict the success or failure outcome $y_i$ of the given prescription or treatment in $g_i$. Embodiments may handle this problem via a kernelized support vector machine (Kernel-SVM) with a graph kernel as described below.

Figure 6:
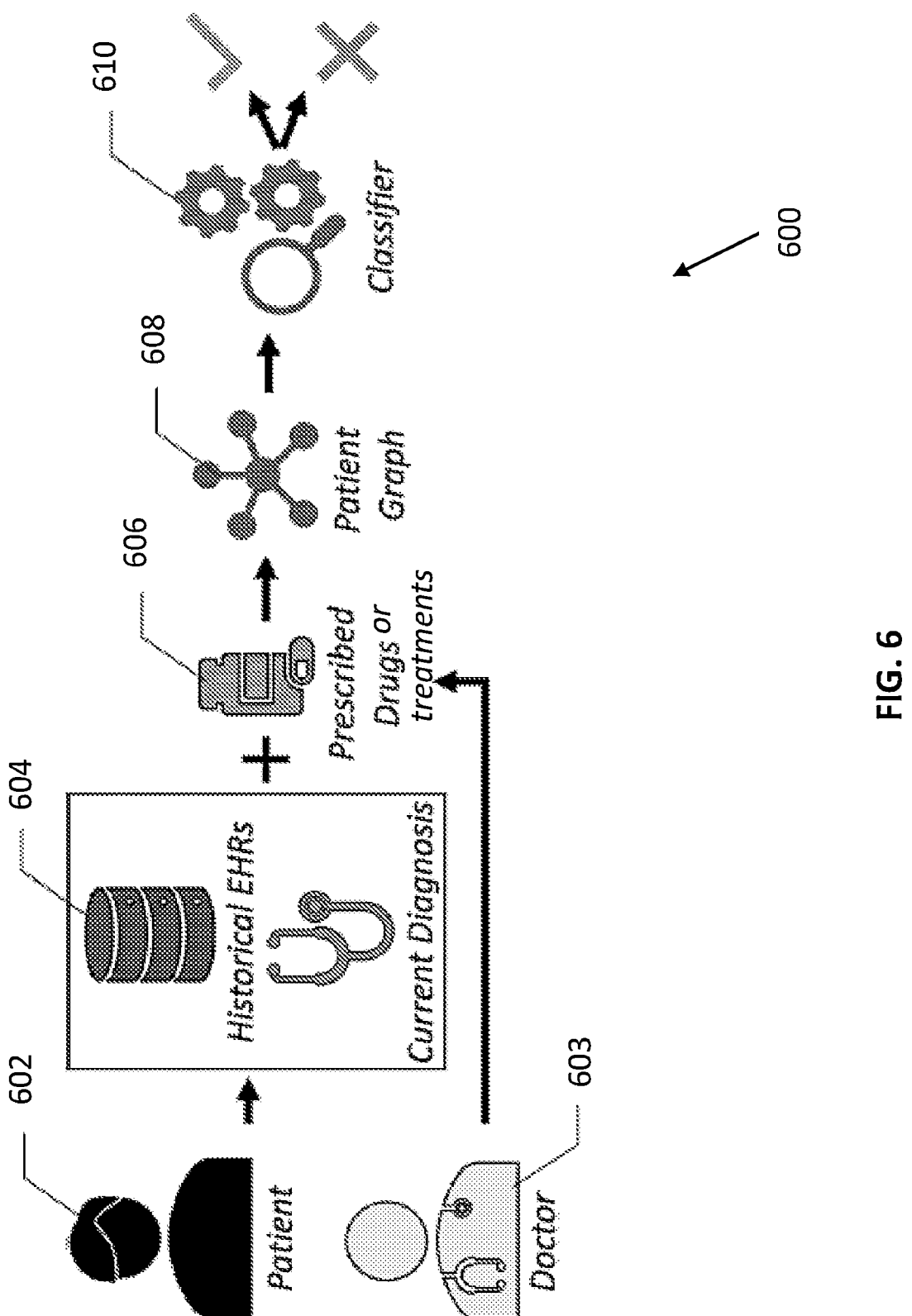
FIG. 6 is an exemplary illustration of a predictive framework directed to predicting effectiveness of a prescribed drug or treatment, according to embodiments of the present systems and methods.

An exemplary embodiment of a predictive framework 600 directed to predicting effectiveness of a prescribed drug is shown in FIG. 6. Predictive framework 600 may include information relating to a patient 602, such as historical patient healthcare records, information from a doctor 603, the current diagnosis 604 and the prescribed drug 606, which is used to generate a patient graph 608, as described above, and then to generate a classifier model 610, which is used to predict effectiveness of the prescribed drug.

In embodiments, a patient healthcare record-based graph kernel may include a Temporal Topological Kernel. To provide an effective treatment, considering the temporal relationships between medical events is necessary. Embodiments may utilize a temporal topological kernel $K_{tp}$. Specifically, input graphs are transformed to shortest path graphs and define the kernel function as follows:

Definition 2 (Temporal topological kernel). Let $g_1=(V_1, E_1)$ and $g_2=(V_2,E_2)$ denote the shortest path graph of $P_{g1}$ and $P_{g2}$ by using the transformation discussed above, a temporal topological kernel $K_{tp}$ is defined as:

$$K_{tp}(g_1, g_2) = \sum_{e_1 \in E_1, e_2 \in E_2} K_{ts}(e_1, e_2) \tag{4}$$

where $K_{ts}$ is a temporal substructure kernel defined on edges $e_1=(u_1, v_1)$ and $e_2=(u_2, v_2)$ which calculates temporal similarity on substructures that connect to nodes in $e_1$, $e_2$.

The intuition of $K_{tp}$ is based on calculating the similarity among temporal ordering on substructures (e.g., node neighborhoods) by $K_{ts}$ between input graphs, recursively. If two graphs are similar, their temporal order for node neighborhood structures are similar. That is, for a given pair of nodes $v_1$, $v_2$ from two similar graphs $g_1$, $g_2$, the time difference from other nodes $u_i$, $u_j$ in $g_1$, $g_2$ to $v_1$, $v_2$ where $u_i$, $u_j$ lie in the subtrees that connect to $v_1$, $v_2$ must be similar.

Definition 3 (Temporal substructure kernel). Given a pair of edge $e_1=(u_1, v_1)$, $e_2=(u_2, v_2)$, their associated edge weight function $w_1$, $w_2$ of $g_1$, $g_2$, and set of neighbor nodes $N_1$,$N_2$ of $u_1$, $u_2$, a temporal substructure kernel $K_{ts}$ is defined as:

$$K_{ts}(e_1, e_2) = \sum_{\substack{e_i=(n_i, u_i) \in E_1, n_i \in N_1 \\ e_j=(n_j, u_2) \in E_2, n_j \in N_2}} K_{ts}(e_i, e_j) \tag{5}$$

$$K_{time}(w_1(e_1), w_2(e_2)) \times K_{node}(u_1, u_2) \times K_{node}(v_1, v_2)$$

and base case definition for the recursion part in Equation 5 when $u_1$ or $u_2$ is the root node:

$$K_{ts}(e_1, e_2) = K_{time}(w_1(e_1), w_2(e_2)) \times K_{node}(u_1, u_2) \times K_{node}(v_1, v_2), \tag{6}$$

where $K_{time}$ is defined as:

$$K_{time}(w_1(e_1), w_2(e_2)) = e^{-1 \times |w_1(e_1) - w_2(e_2)|}, \tag{7}$$

and $K_{node}$ is defined as:

$$K_{node}(u_1, u_2) = \begin{cases} 1, & \text{if label}(u_1) = \text{label}(u_2) \\ 0, & \text{otherwise} \end{cases} \tag{8}$$

To show $K_{ts}$ is a valid kernel, it must be shown that it is positive definite.

Proof. $K_{node}$ is a Dirac delta function which is proven to be positive definite. $K_{time}$ is positive definite since the transformation of an exponential function is positive definite. It is known that positive definiteness is closed under positive scalar linear combination and multiplication on positive definite kernels, and it holds in the base case definition in Equation 6. As a result, $K_{ts}$ is positive definite, and $K_{tp}$ is therefore positive definite.

Figure 7:
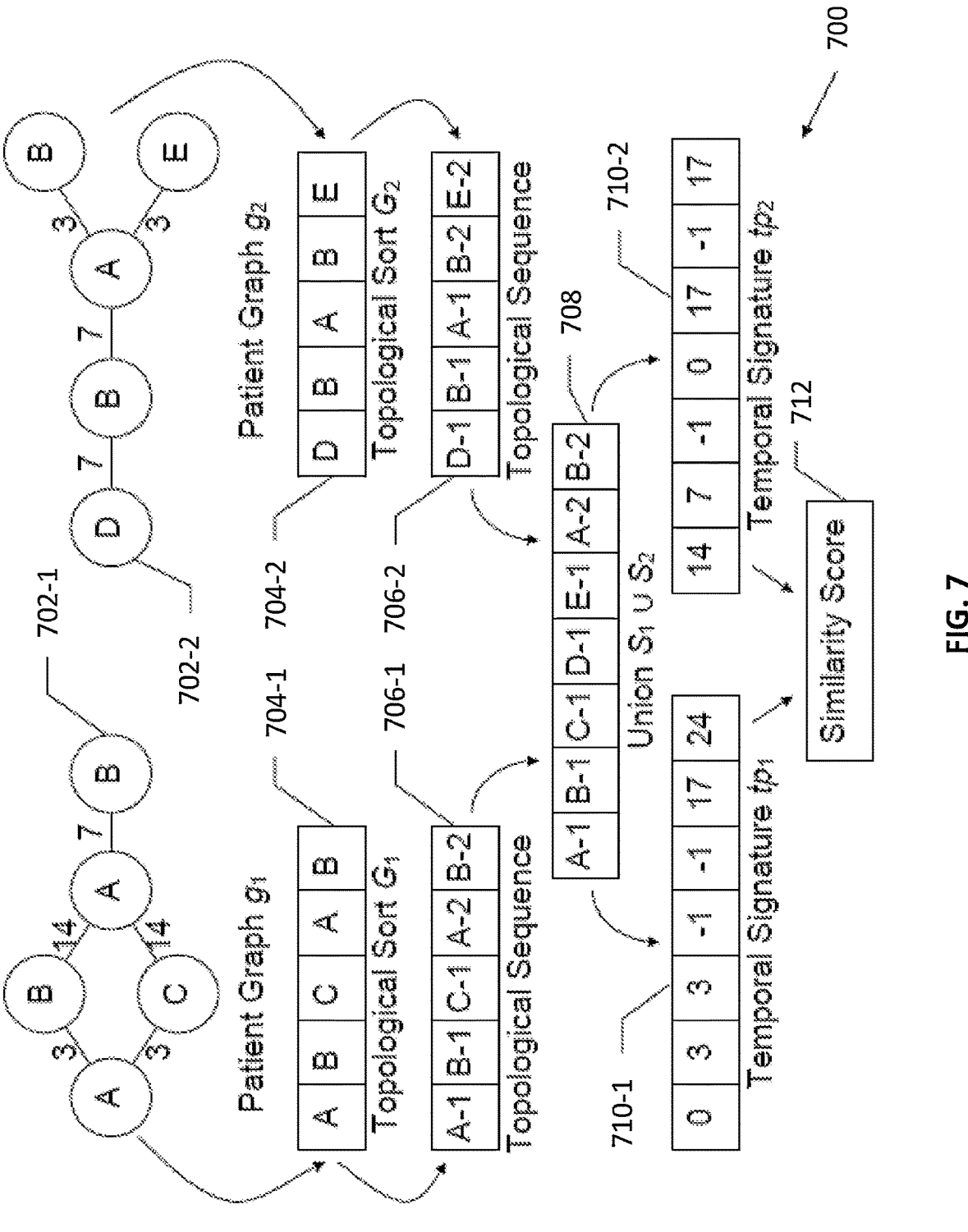
FIG. 7 is an exemplary flow diagram of a process of transferring the input from patient graphs to temporal signatures, according to embodiments of the present systems and methods.

Embodiments may, for a given pair of graph input $g_1$, $g_2$, calculate their kernel value via a kernel function. In embodiments, a patient healthcare record-based graph kernel may include a Temporal proximity kernel, which requires definition of a Topological sequence and a Temporal signature. An exemplary flow diagram of a process 700 of transferring the input from patient graphs to temporal signatures is shown in FIG. 7. As shown in FIG. 7, process 700 begins with patient graphs $g_1$ 702-1, $g_2$ 702-2. At 704-1, 704-2, a topological sort is performed on each patient graph $g_1$ 702-1, $g_2$ 702-2 to form topological sequences 706-1, 706-2.

To define a topological sequence 706-1, 706-2, let T be a topological ordering of graph $$G = (V, E) \text{ such that } T = \{n_i \mid i = 1, \dots, |V|\}, \text{ the topological sequence } S \text{ is defined as } S = \{n_i \cdot \text{label} + \text{level} \mid i = 1, \dots, |V|, \text{ and } n_i \in T\} \qquad (9)$$

where+represents the string concatenation and level denotes the order of occurrence of label associated to node n; in T. Namely, every node in the topological sequence has an attached number to indicate the level. The level indicates the order of occurrence of the same node label in the topological ordering.

At 708, unions of topological sequences 706-1, 706-2 are performed to generate temporal signatures 710-1, 710-2. To define a topological signature, let $S_1$, $S_2$ be topological sequences of two input graphs $g_1$, $g_2$, and $S = S_1 \cup S_2$ with the union set length $m = |S|$. Define the temporal signature for $g_1$ as $tp_1 = \{v_{11}, \dots, v_{1m}\}$ where $$v_{1_j} = \begin{cases} d_j, & \text{if } S[j] \in S_1 \\ -1, & \text{otherwise} \end{cases}, \text{ for } j = 1, \dots, m \qquad (10)$$

and define the temporal signature for $g_2$ as $tp_2 = \{v_{21}, \dots, v_{2m}\}$ where $$v_{2_j} = \begin{cases} d_j, & \text{if } S[j] \in S_2 \\ -1, & \text{otherwise} \end{cases}, \text{ for } j = 1, \dots, m \qquad (11)$$

for $d_j$ denotes the total passage day from the root node to node $n_j$ in its belonging patient graph. Thus, $g_1$ 702-1, $g_2$ 702-2 have been transferred into their vector representations $tp_1$ 710-1, $tp_2$ 710-2.

At 712, a similarity score is computed. For example, a temporal proximity kernel $K_{tp}$ may calculate the kernel value between $g_1$, $g_2$ via temporal signature $tp_1$, $tp_2$ as:

$$K_{tp}(g_1, g_2) = e^{-\|tp_1 - tp_2\|} \qquad (12)$$

where $\|tp_1 - t_{p2}\|$ is the Euclidean distance between $tp_1$, $tp_2$.

Figure 8:
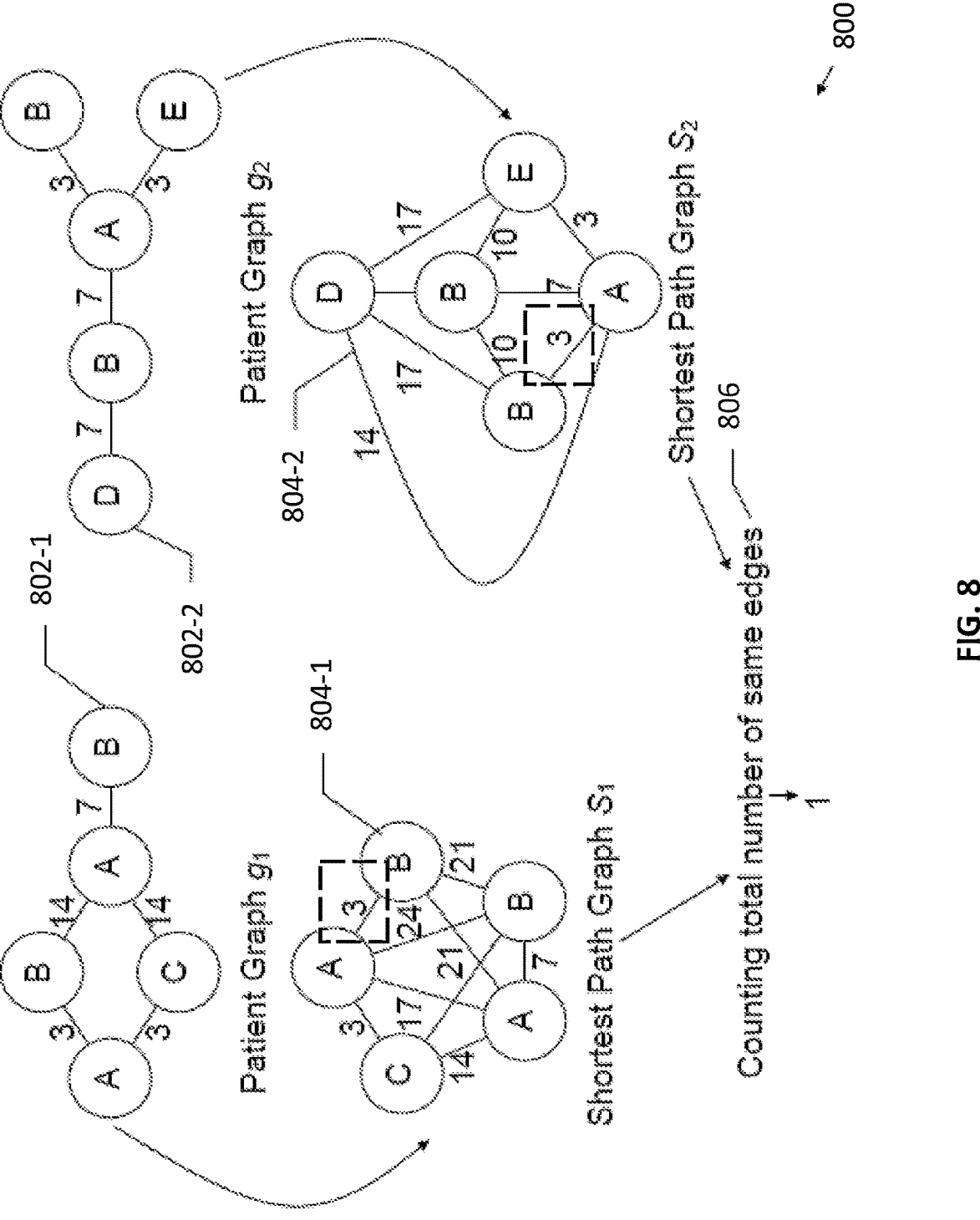
FIG. 8 is an exemplary flow diagram of a process of transferring the input from patient graphs to a shortest path kernel, according to embodiments of the present systems and methods.

An exemplary flow diagram of a process 800 of transferring the input from patient graphs to a shortest path kernel is shown in FIG. 8. As shown in FIG. 8, process 800 begins with patient graphs $g_1$ 802-1, $g_2$ 802-2. At 804-1, 804-2, a shortest path graphs are generated from each patient graph $g_1$ 802-1, $g_2$ 802-2. At 806, a shortest path kernel $K_{sp}$ calculates the edge walk similarity on the shortest path graphs for two input graphs, for example by counting the total number of edges that are the same.

Figure 9:
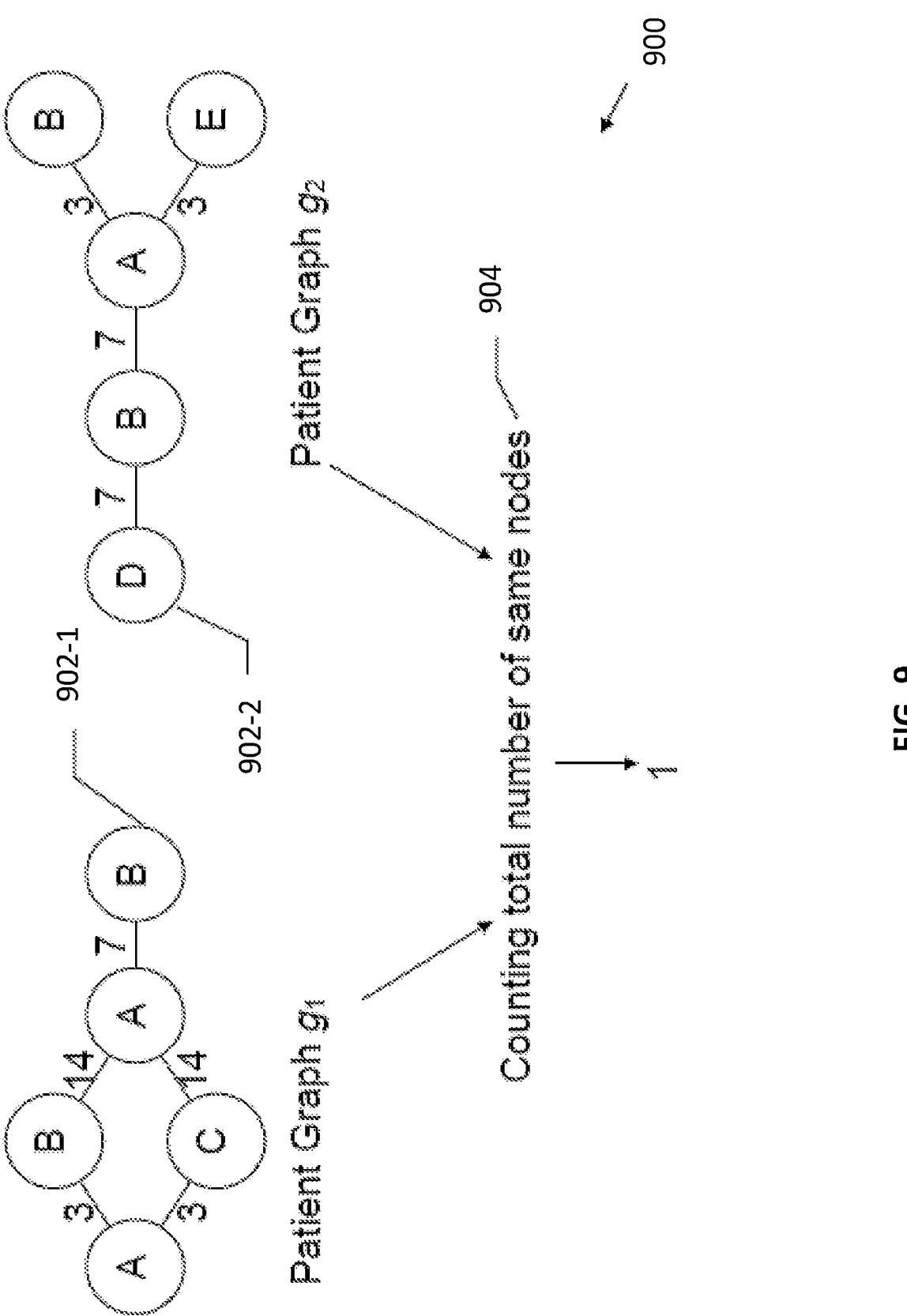
FIG. 9 is an exemplary flow diagram of a process of transferring the input from patient graphs to a node kernel, according to embodiments of the present systems and methods.

An exemplary flow diagram of a process 900 of transferring the input from patient graphs to a node kernel is shown in FIG. 9. As shown in FIG. 9, process 900 begins with patient graphs $g_1$ 902-1, $g_2$ 902-2. At 904, a node kernel $K_{node}$ compares the node labels of two input graphs. The kernel value is the total number of same node labels:

$$K_{node}(g_1, g_2) = \sum_{n_1 \in g_1, n_2 \in g_1.V} K_{label}(n_1, n_2) \qquad (13)$$

where $K_{label}$ is defined as:

$$K_{node}(n_1, n_2) = \begin{cases} 1, & \text{if label}(n_1) = \text{label}(n_2) \\ 0, & \text{otherwise} \end{cases} \qquad (14)$$

Figure 10:
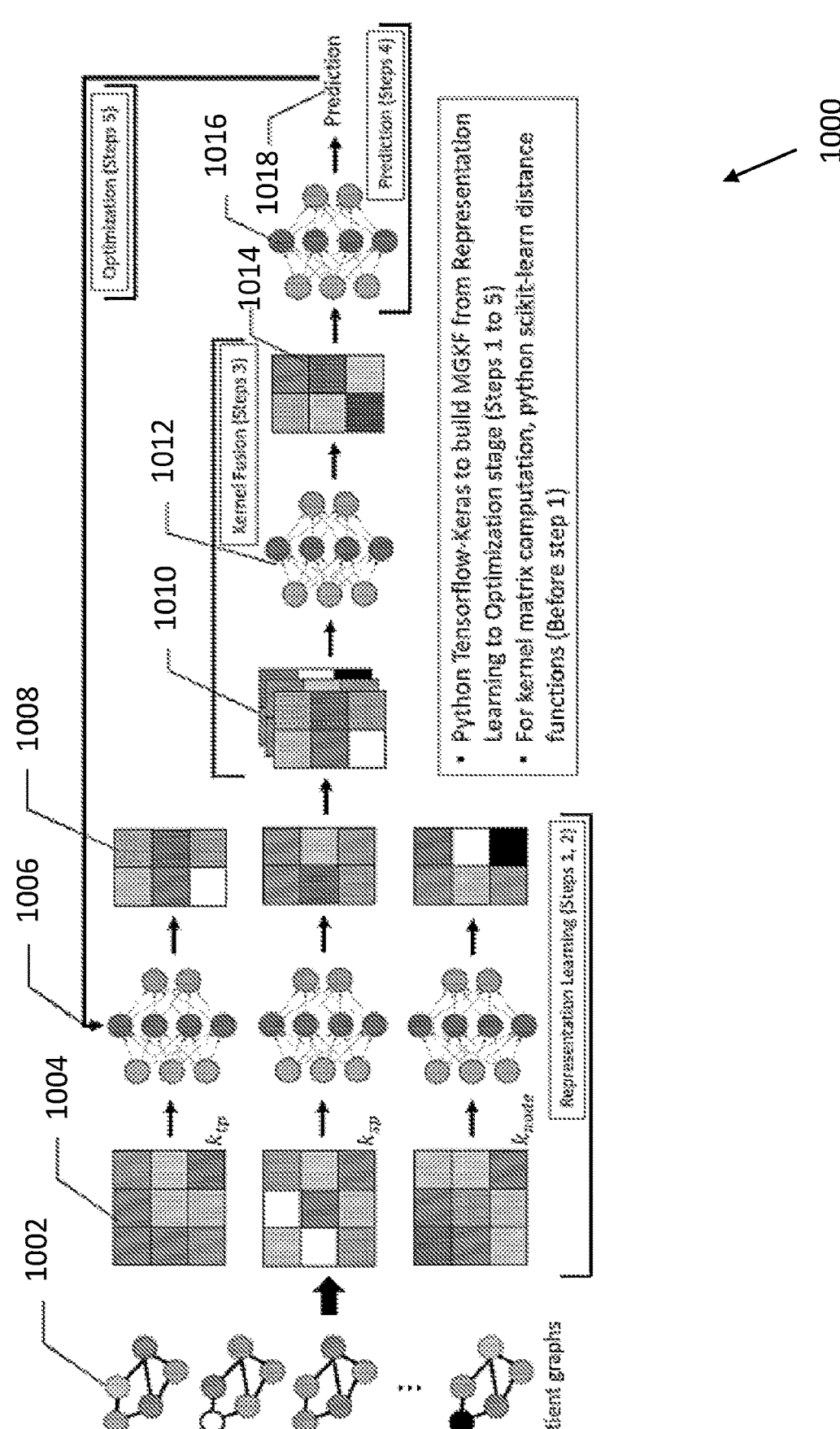
FIG. 10 is an exemplary flow diagram of a process of operation of a multiple graph kernel fusion architecture (MGKF) to perform graph classification, according to embodiments of the present systems and methods.

Embodiments may utilize a multiple graph kernel fusion architecture (MGKF) 800 to perform graph classification, a process of operation of which is shown in FIG. 10. At 1002, a plurality of patient graphs is received/input. At 1004, a plurality of kernel gram matrices is generated. To capture multi-view characteristics on patient graphs, two additional kernels are used—the shortest path kernel and the node kernel, in conjunction with the temporal proximity kernel. The best combination of these kernels is found in an end-to-end manner. Specifically, temporal proximity kernel $K_{tp}$ focuses on temporal similarity between substructure such as node ordering and their time difference, shortest path kernel $K_{sp}$ aims to capture similarity in overall connection, and node kernel $K_{node}$ offers a balance between local and global similarity by comparing all node labels between two patient graphs to achieve best accuracy as well as prevent overfitting from noise collaboratively by kernels.

Given kernel gram matrices on all pair of n graphs for each kernel type $K_t \in R^{n \times n}$ where $K_t$ $g_i$ $g_j = k_t(g_i, g_j)$ and $t \in \{tp, sp, node\}$, at 1006, a multi-layer perceptron (MLP) is used to perform representation learning to generate the corresponding kernel embedding 1008 representation $g_{emb_t} \in R^{n \times m}$ where $m \ll n$. In this case, each row i in $K_t$ represents a high-dimensional feature vector with each dimension being a kernel value (e.g., similarity score) between its associated graph $g_i$ and all other graphs, and its kernel embedding $g_{emb_i}$ can be treated as a dimension reduction by using traditional kernel approximation techniques to generate low dimensional features for $g_i$ such that efficient linear classifier can be used directly. $g_{i_t} \in R^n$ is converted to $g_{emb_t} \in R^m$ under kernel type t as follows:

$$g_{emb_t} = \text{ReLU}(W_t g_{i_t} + b_t) \qquad (15)$$

by using the kernel embedding weight matrix $W_t \in R^{m \times n}$ and the bias vector $b_t \in R^m$ where n is the number of input graphs, and m is the dimension for the embedding space. The rectified linear unit (ReLU) activation is defined as ReLU (val)=max (val, 0). For deep architecture, the layer l is computed with its previous layer l−1 with related parameters $W_{tl}$ and $b_{tl}$ within layer by using the same computation as for the embedding for input kernel gram matrix such as:

$$g_{emb_t} = \text{ReLU}(W_{tl} g_{emb_{t_{l-1}}} + b_{tl}) \qquad (16)$$

At 1010, to combine three kernels, their embeddings 1008 from the last layer is averaged and at 1012 is fused to generate the kernel fusion $g_{emb_F}$ 1014 using another dense layer with ReLU activation that learns the kernel fusion $g_{emb_F} \in \mathbb{R}^f$:

$$g_{emb_{sum}} = \sum_{t \in \{tp, sp, node\}} g_{emb_{t_{last}}} \qquad (17)$$

$$g_{emb_{avg}} = \frac{g_{emb_{sum}}}{3}$$

$$g_{emb_F} = ReLU\left(W_F g_{emb_{avg}} + b_F\right)$$

in which $W_F \in \mathbb{R}^{f \times q}$ is the fusion weight matrix with fusion embedding dimension f and the bias vector $b_F \in \mathbb{R}^f$ assuming the last embedding layer dimension is q.

Further, at 1016, the prediction 1018 of the label of success or failure for $g_{emb_F}$ is produced by using a Sigmoid layer defined as:

$$\hat{y} = \text{Sigmoid}\left(W_p g_{emb_F} + b_p\right) \qquad (18)$$

where $W_p \in \mathbb{R}^{1 \times f}$ and $b_p \in \mathbb{R}$ are trainable weights used to generate class label $\hat{y} \in \{0, 1\}$. A binary cross-entropy loss function is used to optimize the best embedding under the fusion setting to learn all kernel embedding weight matrices.

In embodiments, each row (for example, each patient) depicts a high dimensional feature vector with each dimension corresponding a kernel value to a specific training example. Since the kernel value can be treated as a similarity measurement, the concept in similarity-based classification is used, in which class labels are inferred by a set of most similar training examples, and the top k most similar patients are consulted to get prediction insights based on the nature that features with higher weight contribute more to the result in a linear classifier. Kernel embedding for each kernel type facilitates a refinement of the similarity, reducing the number of training examples used to infer and also reducing the number of input dimensions. Similar patients with allied graph similarity is grouped into one coordinate (e.g., dimension) in the embedding space.

Since kernel embedding space (i.e., a semantic space or semantic map) is trained in an end-to-end manner through ReLU operation in Equation 16, which achieves the interpretability, a set of candidates is selected that contribute most to the prediction, via the top k value coordinates in the embedding space. The selected ones under a different kernel type can be interpreted as multi-view representative cases (such as time propagation or disease connection) in case-based learning. In practice, patient $g_{emb_t}$ is sorted in kernel embedding space, and the top k coordinates are selected. The top k' training examples for the i-th coordinate in top k coordinates are selected. All sorts are in a reverse order:

$$\text{argsort}\left(g_{emb_t}\right)[1:k] \qquad (19)$$

$$\text{argsort}\left(W_t[i,:]\right)[1:k'] \qquad (20)$$

Figure 11:
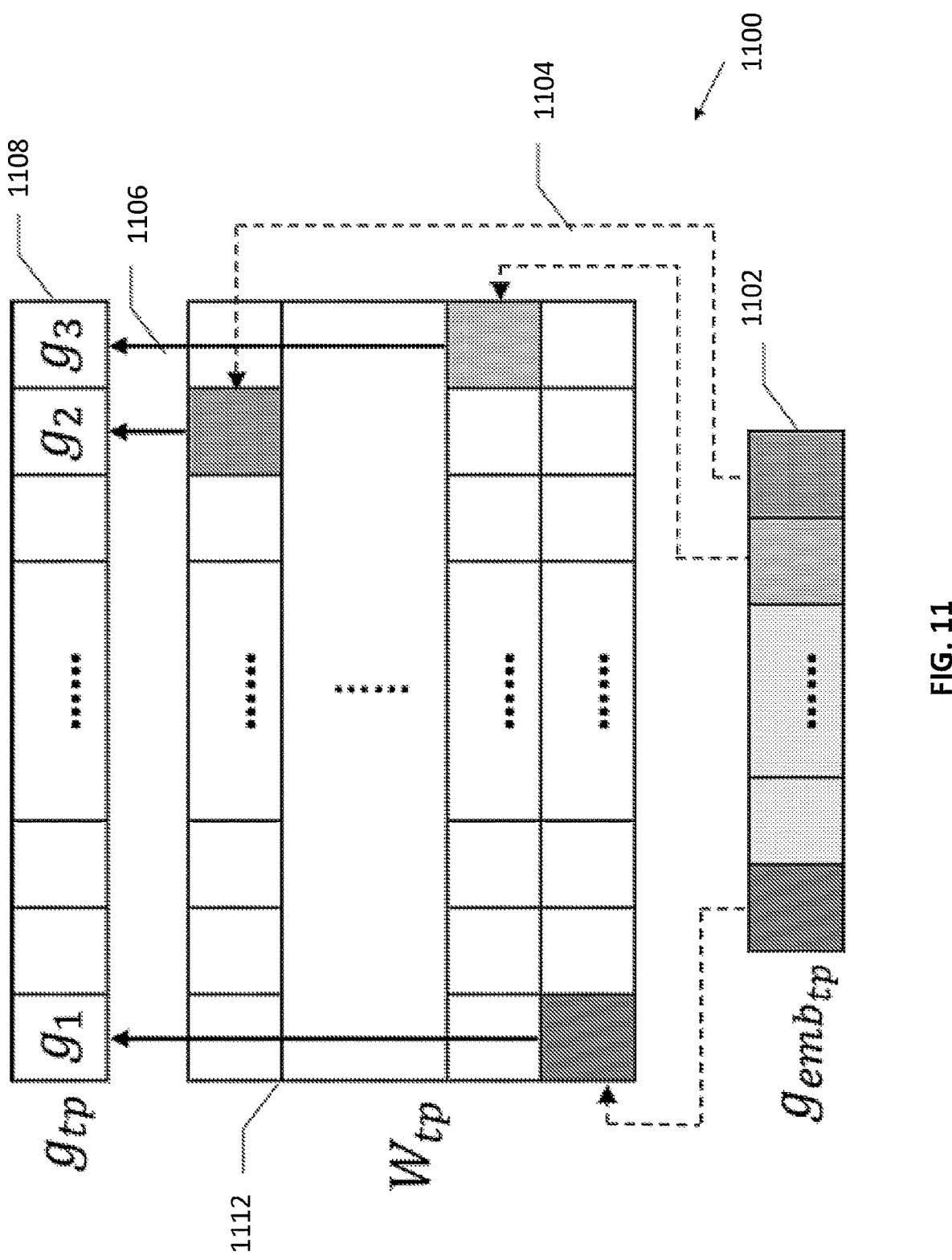
FIG. 11 is an exemplary flow diagram of a process of interpretation, according to embodiments of the present systems and methods.

An exemplary process 1100 of interpretation is shown in FIG. 11. Given an embedded patient vector $g_{emb_{tp}}$ 1102, at 1104, it is sorted in a descending order and, for example, the top three value dimensions are selected. At 1106, the training examples in $g_{tp}$ 1108 that contribute most is found, through weight matrix $W_{tp}$ 1112.

Figure 12:
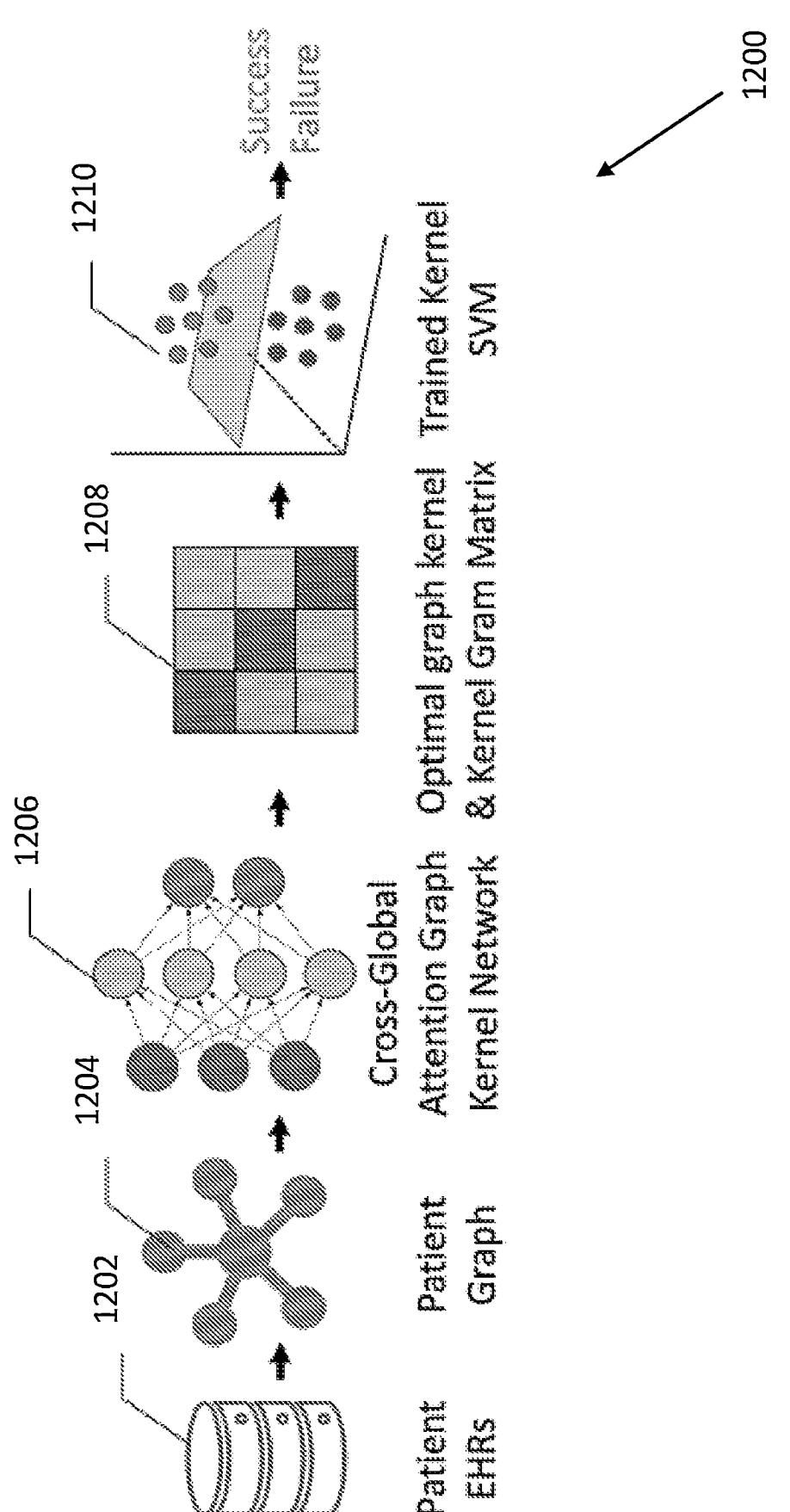
FIG. 12 is an exemplary illustration of a predictive framework directed to predicting effectiveness of a course of treatment for a chronic condition, according to embodiments of the present systems and methods.

An exemplary embodiment of a predictive framework 1200 directed to predicting effectiveness of a course of treatment for a chronic condition is shown in FIG. 12. Predictive framework 1200 may include information relating to an anonymous patient 1202, such as patient healthcare records, which is used to generate a patient graph 1204, as described above. Patient graph 1204 is used to generate a Cross-Global Attention Graph Kernel Network 1206, which is used to generate an optimal graph kernel and Kernel Gram Matrix 1208 which is used to generate a trained Kernel SVM 1210, which is used to predict the effectiveness of the course of treatment.

Embodiments may formulate the prediction task as a binary graph classification on graph-based patient healthcare records 1204 using a kernel SVM 1210. Such embodiments may learn a graph kernel. Given a set of success and failure case patient graphs G, a deep neural network may learn an optimal graph kernel k. Then, the prediction for success or failure is performed by a kernel SVM 1210 using a kernel gram matrix K 1208 such that $K_{ij} = k(G_i, G_j)$ where $G_i, G_j \in G$. For an incoming patient, a patient graph $G_p$ 1204 is created based on the concatenation of patient's medical history, current diagnosis, and treatment plan. Then, the kernel value between $G_p$ and all training examples $G_i \in G$ is determined, and prediction is performed through a kernel SVM 1210, as shown in FIG. 12.

Figure 13:
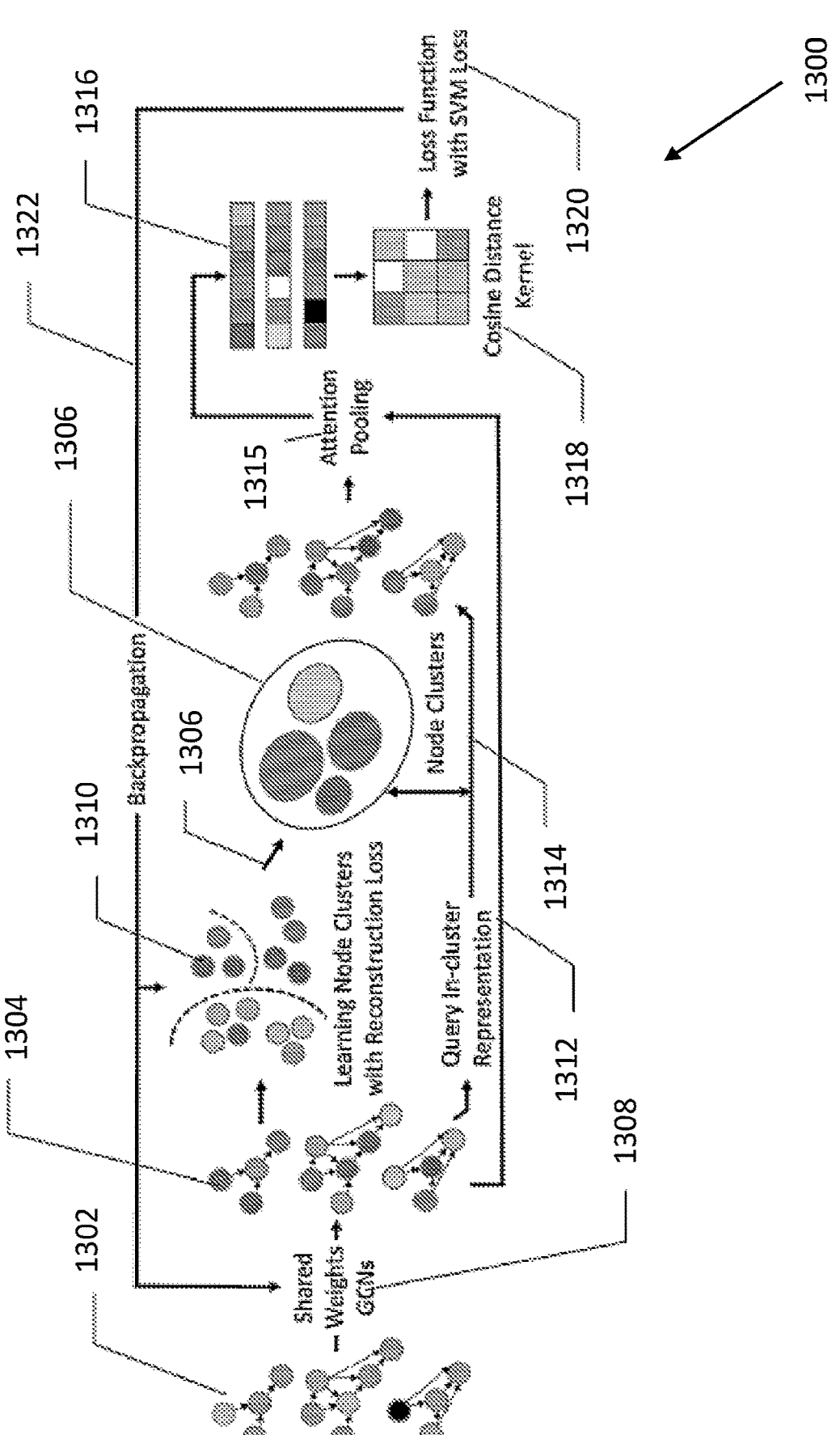
FIG. 13 is an exemplary illustration of a Cross-Global Attention Graph Kernel Network learning an end-to-end deep graph kernel on a batch of graphs, according to embodiments of the present systems and methods.

In embodiments, a Cross-Global Attention Graph Kernel Network 1100 may learn an end-to-end deep graph kernel on a batch of graphs, as shown in FIG. 13. At 1302, a plurality of patient graphs is received/input. The node level embedding 1304 and node clusters 1306 is determined first by, at 1308 determining shared weight Graph Convolutional Networks (GCNs) to form node level embedding 1304, and at 1310, determining learning node clusters with reconstruction loss to form node clusters 1306. The graph level embedding is derived 1312 from node matching 1314 based attention pooling 1315. The loss 1320 is calculated 1316 by the resulting distance and kernel matrix 1318 and backpropagation 1122 is performed to update all model parameters.

As shown, this is accomplished through cross-global attention node matching without an explicit pairwise similarity computation. Given a batch B of input graphs $G_1, \ldots, G_{|B|}$ with batch size |B|, their nodes are embedded into a lower dimensional space, where node structures and attribute information are encoded in vectors. A graph level embedding may then be produced by a graph pooling operation on node level embedding via cross-global attention node matching. The batchwise cosine distance is calculated and a kernel gram matrix is generated on the entire batch of resulting graph embedding. Finally, the network loss is computed with contrastive loss, kernel alignment, and SVM primal objective.

Embodiments may perform Graph Embedding using Graph Convolutional Networks. Graph Convolutional Networks (GCN) may perform 1-hop neighbor feature aggregation for each node in a graph. The resulting graph embedding is permutation invariant when a pooling operation is properly chosen. Given an n number of nodes patient graph G with node attribute one-hot vector matrix $X \in \mathbb{R}^{n \times c}$, where c denotes the total number of medical codes in patient healthcare records, and a weighted adjacency matrix $A \in R^{n \times n}$, GCN is used to generate a node level embedding $H \in R^{n \times d}$ with embedding size $d \in R$ as follows:

$$H = f\left(\tilde{D}^{-1} \tilde{A} X W\right) \quad (21)$$

where $\tilde{D}$ is the diagonal node degree matrix of $\tilde{A}$ defined with $\tilde{D} = \Sigma j \tilde{A}_{ij}$, $\tilde{A} = A + I$ is the adjacency matrix with self-loops added, $W \in R^{c \times d}$ is a trainable weight matrix, and f is a non-linear activation function such as ReLU (x)=max (0, x). The embedding H can be an input to another GCN, creating stacked multiple graph convolution layers:

$$H^{k+1} = f\left(\tilde{D}^{-1} \tilde{A} H^k W^k\right), H^0 = X \quad (22)$$

where $H^k$ is the node embedding after the $k^{th}$ GCN operation, and $W^k$ is the trainable weight associated with the $k^{th}$ GCN layer. The resulting node embedding $H^{k+1}$ contains k-hop neighborhood structure information aggregated by graph convolution layers.

Embodiments may perform graph embedding using higher-order graph information. To capture longer distance nodes and their hierarchical multi-hop neighborhood information, t multiple GCN layers are stacked and all layer's outputs $H^{1:t} = [H^1, \ldots , H^t]$ concatenated, where $H^{1:t} \in R^{n \times (t \times d)}$. The concatenated node embedding might be very large and could potentially cause a memory issue for subsequent operations. To mitigate such drawbacks, a non-linear transformation is performed on $H^{1:t}$ by a trainable weight $W_{concat} \in R^{(t \times d) \times d}$ and a ReLU activation function as follows:

$$H_{final} = ReLU\left(H^{1:t} W_{concat}\right) \quad (23)$$

To produce the graph level embedding, instead of using another type of pooling operation, embodiments may use cross-global attention node matching and its derived attention-based pooling.

Cross-Global Attention Node Matching between graphs is computed via a pairwise node similarity measurement. This optimizes a distance metric-based or KL-divergence loss on the graph pairs or triplets necessitating vast training pairs or triplets to capture the entire global characteristics. One way to avoid explicit pair or triplet generation utilizes efficient batch-wise learning via optimizing classification loss. However, pairwise node matching in a batch-wise setting is problematic due to graph size variability. To address this issue, one may use a batch-wise attention-based node matching scheme, also known as cross-global attention node matching. The matching scheme may learn a set of global node clusters and may compute the attention weight between each node and the representation associated with its membership cluster. The pooling operation based on its attention score to global cluster may perform a weighted sum on nodes to derive a single graph embedding.

Given node embedding $H_{final} \in R^{n \times d}$ from the last GCN layer and transformation after concatenation in Equation 23, define $M \in R^{s \times d}$ as a trainable global node cluster matrix with s clusters and d dimension features sized to provide an overall representation of its membership nodes. Here, mem bership assignment is defined by $A \in R^{n \times s}$ for H final and as follows:

$$A = \text{Sparsemax}\left(ReLU\left(H_{final} M^T\right)\right) \quad (24)$$

where Sparsemax is a sparse version Softmax (see below), that outputs sparse probabilities. It can be treated as a sparse soft cluster assignment. A is interpreted as a cluster membership identity with s dimension feature representation. Further define the query of nodes' representation in their belonging membership cluster:

$$Q = \text{Tanh}(AM) \quad (25)$$

where $Q \in R^{n \times d}$ denotes a queried representation for each node in $H_{final}$ from their belonging membership cluster. As shown in FIG. 12, matching can be treated as retrieving cluster identity from global node clusters, and similar nodes are assigned to a similar or even the same cluster membership identity. To construct a better cluster, an auxiliary loss is added by minimizing the reconstruction error $L_{recon} = \|H_{final} - Q\|F$, which is similar to Non-negative Matrix Factorization (NMF) clustering.

Embodiments may utilize Pooling with Attention-based Node Matching. The intuition of pairwise node matching is to assign higher attention-weight to those similar nodes. In other words, matching occurs when two nodes are highly similar, closer to each other than to other possible targets. Following this idea, it is observed that two nodes are matched if they have similar or even identical cluster membership. The higher the similar membership identity, the higher the degree of node matching. In addition, a cluster is constructed by minimizing the reconstruction error between the original node H final and the query representation Q. A node with high reconstruction error means no specific cluster assignment and further lowers the chance to match other nodes. This can be measured by using similarity metrics (e.g., cosine similarity) between $H_{final}$ and Q. Based on these observations, cross-global attention node matching pooling is designed, wherein a node similar to the representation in its cluster membership should receive higher attention weight, as follows:

$$a = \text{Softmax}\left(Sim(H_{final}, Q)\right) \quad (26)$$

$$G_{emb} = \sum_{i=1}^{n} a_i H_{final_i} \quad (27)$$

where $\alpha \in R^n$ is the attention weight for each node, Softmax is applied to generate importance among nodes by using Sim, a similarity metric (e.g., cosine similarity), and the resulting pooling $G_{emb}$ is the weighted sum of node embeddings that compress higher order structure and node matching information from other graphs.

Figure 14:
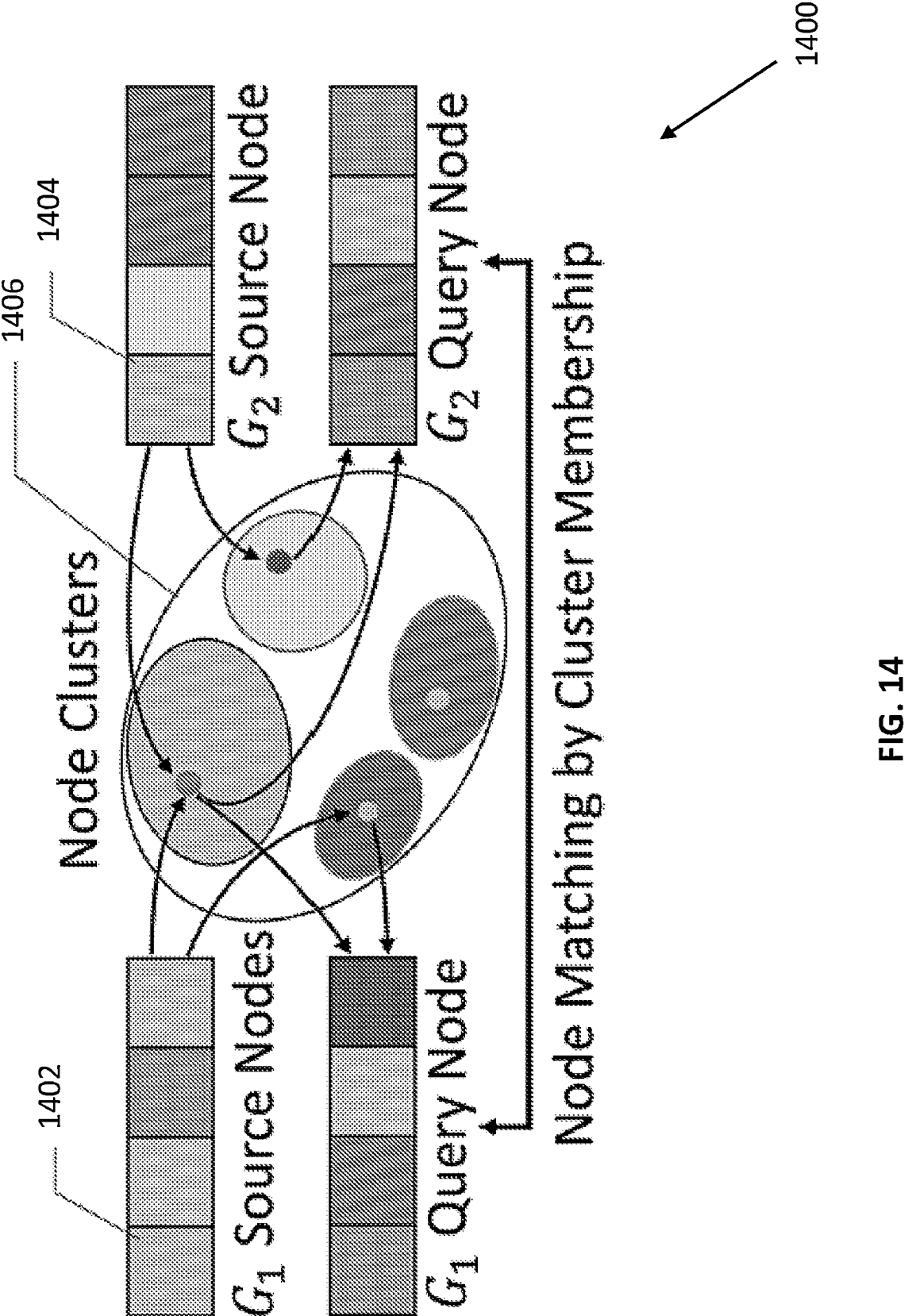
FIG. 14 is an exemplary illustration of matching by retrieving cluster identity from global node clusters, according to embodiments of the present systems and methods.

Matching and cluster assignment membership is illustrated in FIG. 14, which shows a predictive framework 1400. Each node in $G_1$ 1402, $G_2$ 1404 may map to a cluster 1406. Their cluster membership assignments may generate their query, which is their representation in terms of belonging to a cluster. Such an assignment is seen as a soft label of cluster membership identity. Similar query means similar cluster membership identity, inducing possible matching.

Graph Kernel. Given a graph pair with their graph level embeddings $G_{emb_1}$, $G_{emb_2}$, the graph kernel is defined as follows:

$$Dist_C\left(G_{emb_1}, G_{emb_2}\right) = 1 - \frac{G_{emb_1} \cdot G_{emb_2}}{\left\|G_{emb_1}\right\|\left\|G_{emb_2}\right\|}$$

$$Dist_E\left(G_{emb_1}, G_{emb_2}\right) = \left\|G_{emb_1} - G_{emb_2}\right\|_2$$

$$K\left(G_{emb_1}, G_{emb_2}\right) = \exp\left(-Dist\left(G_{emb_1}, G_{emb_2}\right)^2\right)$$

where $Dist_C$ is a cosine distance and $Dist_E$ is the Euclidean distance. Dist can be either $Dist_C$ or $Dist_E$. The resulting kernel function is positive definite since $\exp(-x)$ is still positive definite for any non-negative real number x. Cosine distance enjoys benefits in more complex data representations. Euclidean distance considers vector magnitude (such as the norm) during measurement which is not sufficiently sensitive to highly variant features such as long-term disease progressions. Moreover, cosine distance can measure objects on manifolds with nonzero curvature such as spheres or hyperbolic surfaces. In general, Euclidean distance can only be applied to local problems which may not be sufficient to express complex feature characteristics. The resulting cosine guided kernel is more expressive, and thus, capable of performing implicit high dimensional mapping. Note that the use of other distance functions that support a positive definitive kernel is likewise within the scope of this disclosure, Given a batch B of input graphs and their class labels $y \in R^{|B|\times 1}$ where $y_i \in \{1, 0\}$, their graph level embeddings are obtained for the entire batch via shared weight GCN with cross-global node matching pooling. Then, their batch-wise distance matrix $D \in R^{|B|\times|B|}$ and batch-wise kernel gram matrix $K \in R^{|B|\times|B|}$ are calculated. The model can be trained by mini-batch Stochastic Gradient Descent (SGD) without training pair and triplet generation. To learn an optimal graph embedding, which results in an optimal graph kernel, it is optimized by contrastive loss with a margin threshold $\lambda > 0$ and kernel alignment loss:

$$\mathcal{L}_{contrastive} = \frac{1}{|B|} \sum_{i,j \in B} (1 - Y_{ij})\max(0, \lambda - D_{ij})^2 + Y_{ij}D_{ij} \quad (28)$$

and kernel alignment loss:

$$\mathcal{L}_{alignment} = \frac{1}{|B|} \sqrt{2 - 2(\langle K, Y \rangle_F / \sqrt{\langle K, K \rangle_F \langle Y, Y \rangle_F}} \quad (29)$$

where $\rangle \cdot, \cdot \langle$ F denotes the Frobenius inner product, K is a batch-wise kernel gram matrix, and $Y \in R^{|B|\times|B|}$ where $Y_{ij}=1$ if $y_i=y_j$ else $Y_{ij}=0$. A good distance-metric may induce a good kernel function and vice versa. So, the graph kernel is learned jointly through optimal cosine distance between graphs via contrastive loss with an optimal graph kernel through kernel alignment loss:

$$\mathcal{L}_{kernel} = \mathcal{L}_{contrastive} + \mathcal{L}_{alignment} \quad (30)$$

To align a learned embedding, distance, and kernel to the classification loss in end-to-end training, the SVM primal objective is incorporated with a squared hinge loss function into the objective:

$$\mathcal{L}_{SVM} = C \sum_{i,j \in B} \beta_i \beta_j K_{ij} + \sum_i \max\left(0, 1 - y_i \sum_{j \in B} K_{ij}\beta_j\right)^2 \quad (31)$$

where $C >= 0$ is a user defined inverse regularization constant and $\beta \in R^{|B|\times 1}$ is a trainable coefficient weight vector. The following is the final model optimization problem formulation:

$$\min_{\theta, \beta} \underbrace{\mathcal{L}_{kernel}}_{\theta} + \underbrace{\mathcal{L}_{recon}}_{\theta} + \underbrace{\mathcal{L}_{SVM}}_{\beta} \quad (32)$$

where $\theta$ denotes a set of all trainable variables in graph embedding and $\beta$ is a trainable coefficient weight vector for SVM. Since the training is done by mini-batch SGD, the SVM objective is only meaningful for a given batch. Namely, gradient for $\beta$ in SVM are only relevant for the current batch update as the SVM objective is dependent on the input kernel gram matrix. When training proceeds to the next batch, the kernel gram matrix is different, and the optimized $\beta$ is inconsistent with the last batch status. To resolve this inconsistent weight update problem, treat SVM as a light-weight auxiliary objective (e.g., regularization), encouraging the model to learn an effective graph kernel. In this case, first perform a forward pass-through graph kernel network, then train the SVM by feeding in the kernel gram matrix from the forward pass output until convergence. The positive definiteness of the kernel function guarantees SVM convergence. Once the SVM is trained, treat $\beta$ as a model constant, and $\mathcal{L}_{SVM}$ now acts as a regular loss function. The gradient of $\theta$ can be computed through $\mathcal{L}_{kernel}$, $\mathcal{L}_{recon}$, and $\mathcal{L}_{SVM}$, and the model can perform backpropagation to update $\theta$.

Figure 15:
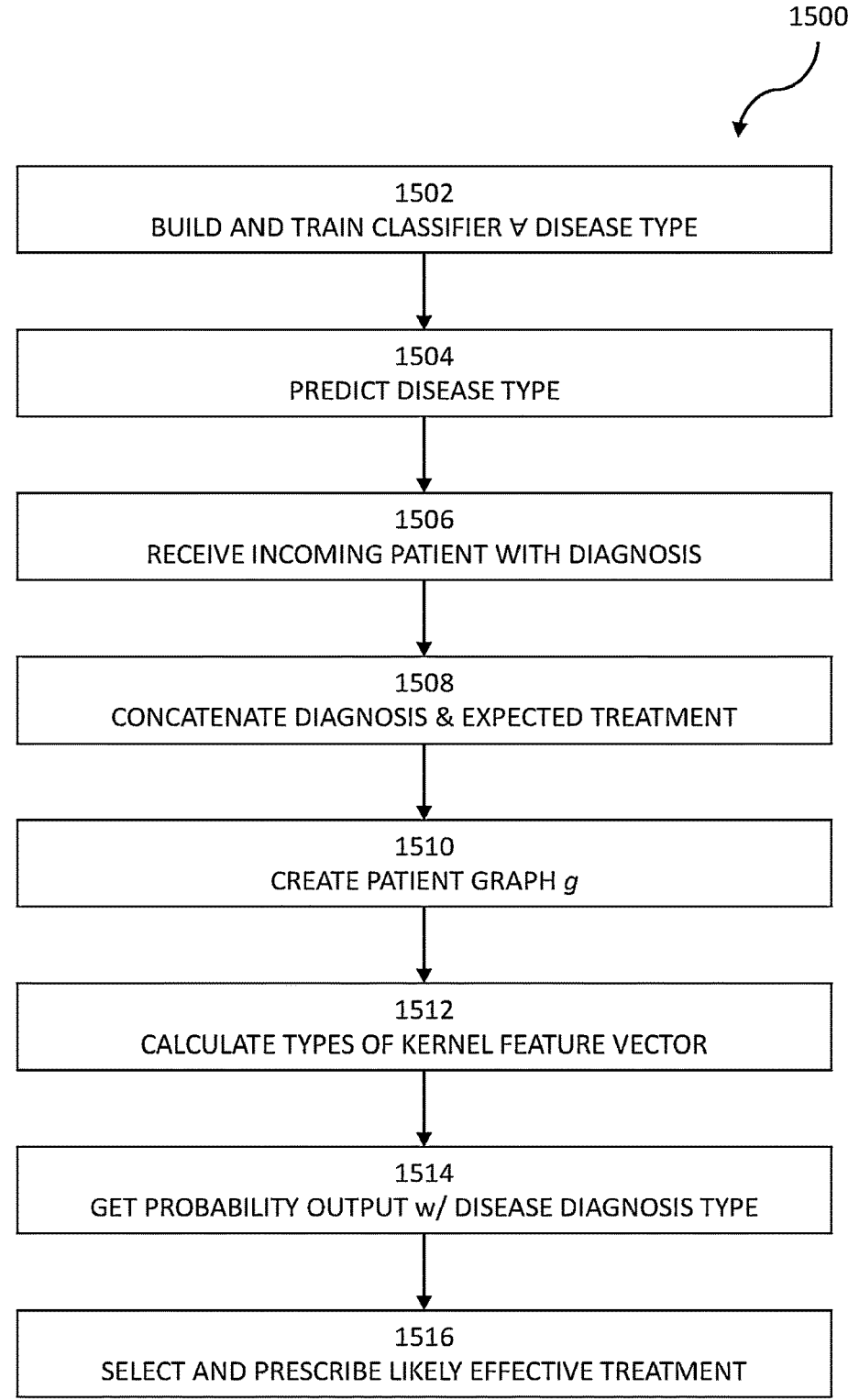
FIG. 15 is an exemplary flow diagram of a process for prediction for outcome of a drug prescription or treatment, according to embodiments of the present systems and methods.

An exemplary process 1500 for predicting the outcome of a treatment is shown in FIG. 15. Process 1500 begins with 1502, in which a classifier with an MGKF (multiple graph kernel fusion) framework is built and trained for each type of disease. Typically, training is performed using only patients with that type of disease to train the MGKF. At 1504, to complete the training, the trained classifier is used with an MGKF framework to perform prediction for each type of disease. At 1506, for an incoming patient with a diagnosis, at 1508 the diagnosis and the expected drug prescription or treatment is concatenated to the patient's medical history (if any). At 1510, a patient graph g is created. At 1512, a plurality of types of kernel feature vectors are calculated between g and all training examples. For example, a Temporal Proximity Kernel, a Shortest Path Kernel, and a Node Kernel is calculated. At 1514, a probability output is obtained using the MGKF with same disease diagnosis type. For example, a probability output >0.5 may mean possible failure. At 1516, a drug or treatment that is likely to be effective, based on the probability output for that drug or treatment is selected and prescribed to a patient.

Figure 16:
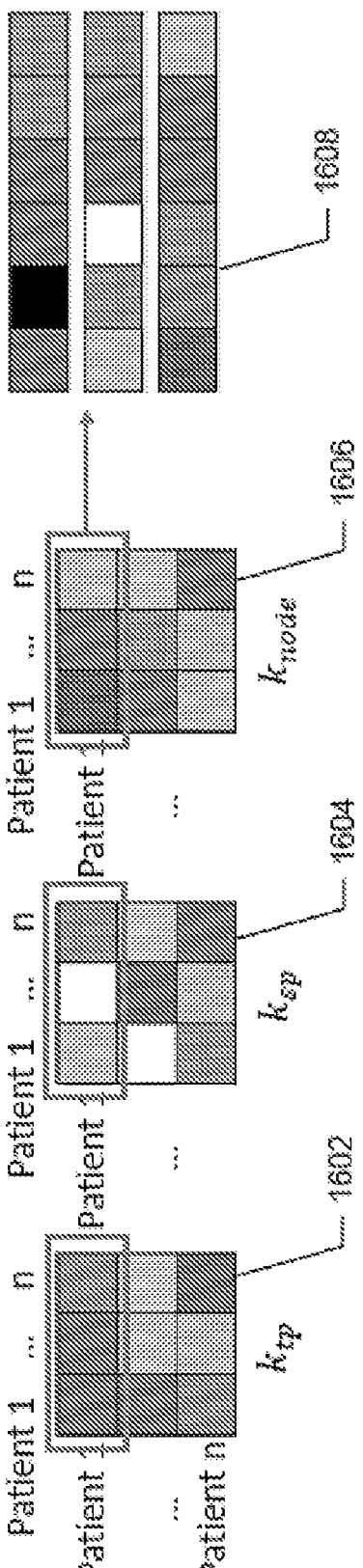
FIG. 16 is an exemplary flow diagram of a process of training a classifier with an MGKF framework, according to embodiments of the present systems and methods.

An exemplary process 1502 of training a classifier with an MGKF framework is shown in FIG. 16. Given n patient graphs under specific type of disease for example, a UTI, an n×n kernel gram matrix is created for each of $k_{tp}$, $k_{sp}$, and $k_{node}$. Each row represents an n dimensional feature vector for each associated patient and describes the similarity (kernel value) to all n patients. In this example, there are n patients with each patient having an n dimensional feature vector in $k_{tp}$, $k_{sp}$, and $k_{node}$. Each row in $k_{tp}$, $k_{sp}$, and $k_{node}$ is treated as a one-dimensional feature vector 1608.

Figure 17:
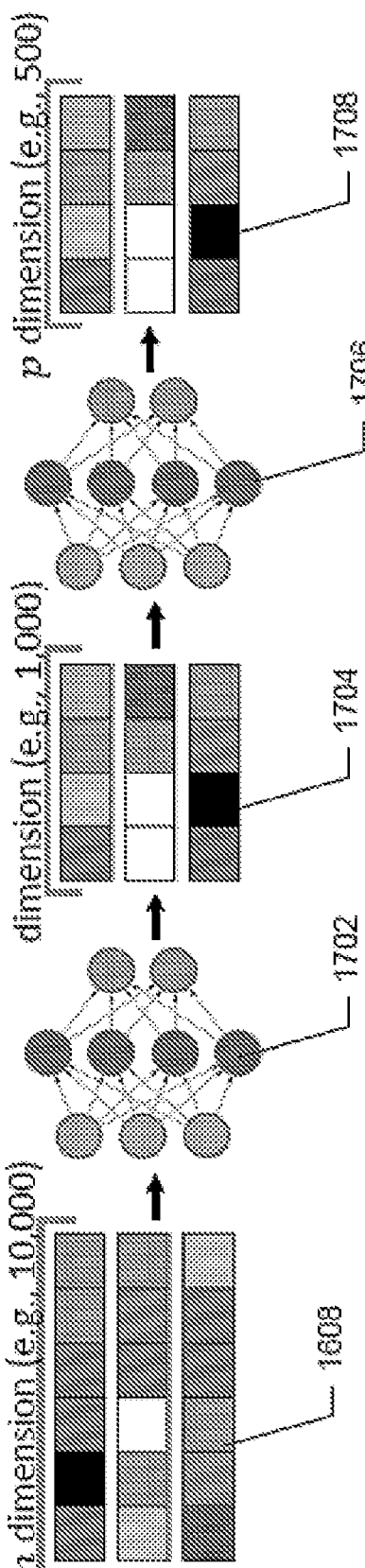
FIG. 17 is an exemplary flow diagram of a portion of a process of using the trained classifiers with an MGKF framework to perform prediction for each type of disease, according to embodiments of the present systems and methods.
Figure 17:
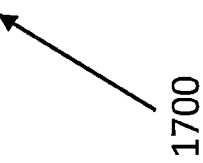
Figure 18:
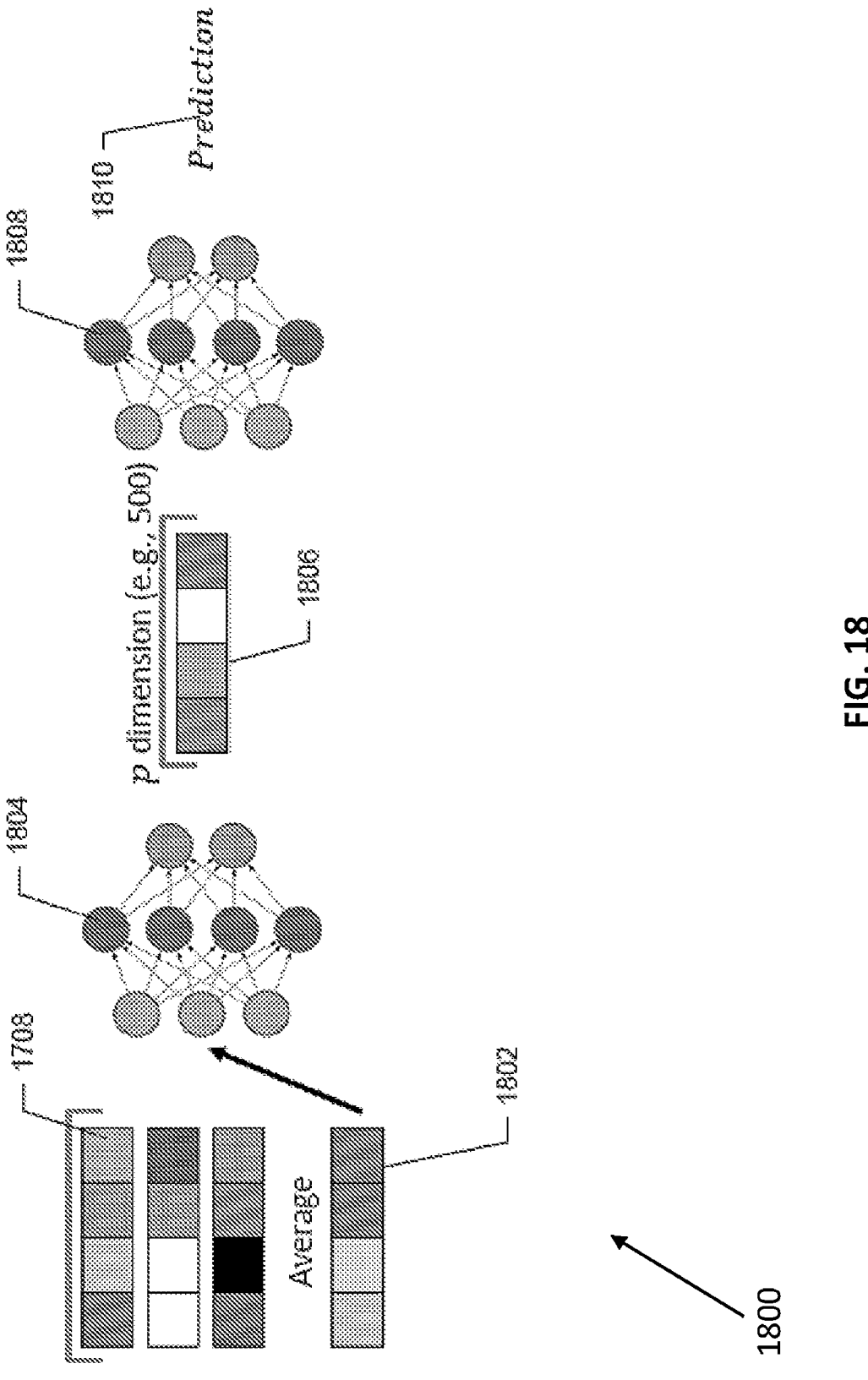
FIG. 18 is an exemplary flow diagram of a portion of a process of using the trained classifiers with an MGKF framework to perform prediction for each type of disease, according to embodiments of the present systems and methods.

An exemplary process 1504, of using the trained classifiers with an MGKF framework to perform prediction for each type of disease is shown in FIGS. 17 and 18. The multiple types of feature vectors (vector of kernel values 1608) is input into an MGKF framework to generate predictions. A portion (representation learning) 1700 of exemplary process 1504 is shown in FIG. 17. For each n dimensional feature vector 1608 from $k_{tp}$, $k_{sp}$, and $k_{node}$, a multilayer perceptron or MLP 1702 is used to reduce the dimension from n to m. For example, at 1702 each type of feature vector is embedded with a dimension size 10,000 to 1,000 1704 via a single layer MLP with ReLU activation (1,000 hidden size). At 1706, for each type of embedding, the dimension may, for example, be reduced from 1,000 to 500 via a 3-layer MLP with ReLU activation (hidden size for 800, 600, and 500 for each layer) to get a final representation 1708.

A portion (Kernel Fusion and Prediction) 1800 of an exemplary process 1504 for disease prediction is shown in FIG. 18. After final representation learning (embedding) 1708 for each type of the feature vectors, the feature vectors are averaged to form a single vector and input into a single layer MLP (500 hidden size) 1804 to learn the final representation 1806. At 1808, another MLP, such as a single layer (1 hidden size) MLP with sigmoid activation is used to output probability 1810 of likelihood for success or failure.

Figure 19:
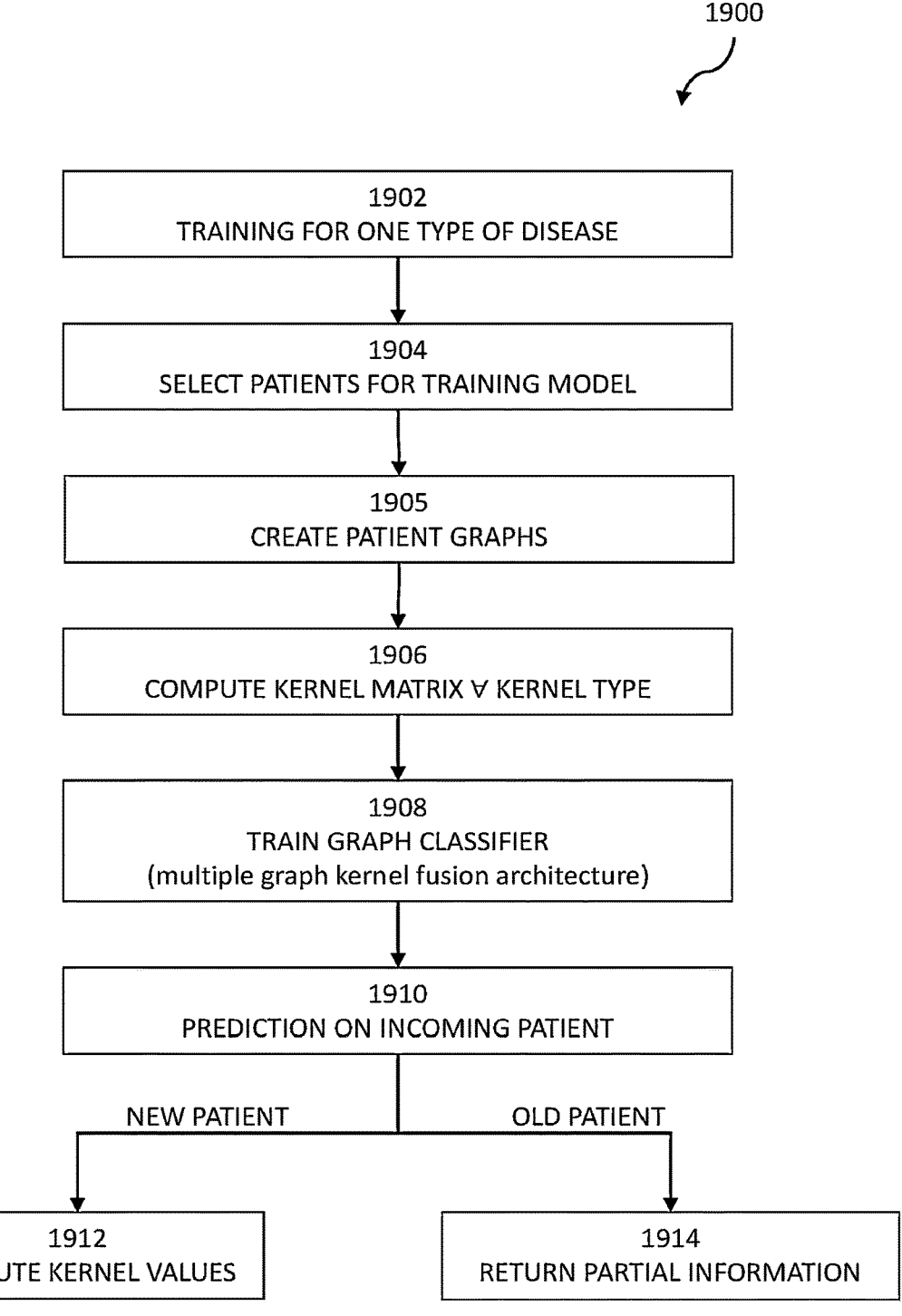
FIG. 19 is an exemplary flow diagram of a process of predicting drug and/or treatment outcomes, according to embodiments of the present systems and methods.

An exemplary process of predicting drug and/or treatment outcomes is shown in FIG. 19. Process 1900 begins with 1902, in which, for training for one type of disease, at 1904, n patients, for example, 10,000, is selected under selected disease types as training examples, and at 1905 their patient graphs are created. At 1906, a pairwise kernel matrix under each type of kernel is computed. For example, a temporal proximity kernel, a shortest path kernel, and a node kernel, may be computed, for all patients. At 1908, the pairwise kernel matrix is input to train the MGKF. At 1910, predictions for incoming patients are generated. At 1912, if the patient is a new patient, that is, not included in the training examples, then the kernel values between the graph of the new patient and all training examples are computed. If the patent is an old patient, that is, included in the training examples, then return the entire patient's belonging row in the kernel gram matrix $k_{tp}$, $k_{sp}$, and $K_{node}$. It is noted that there is no need to retrain when there is a sufficiently large number of training examples.

Figure 20:
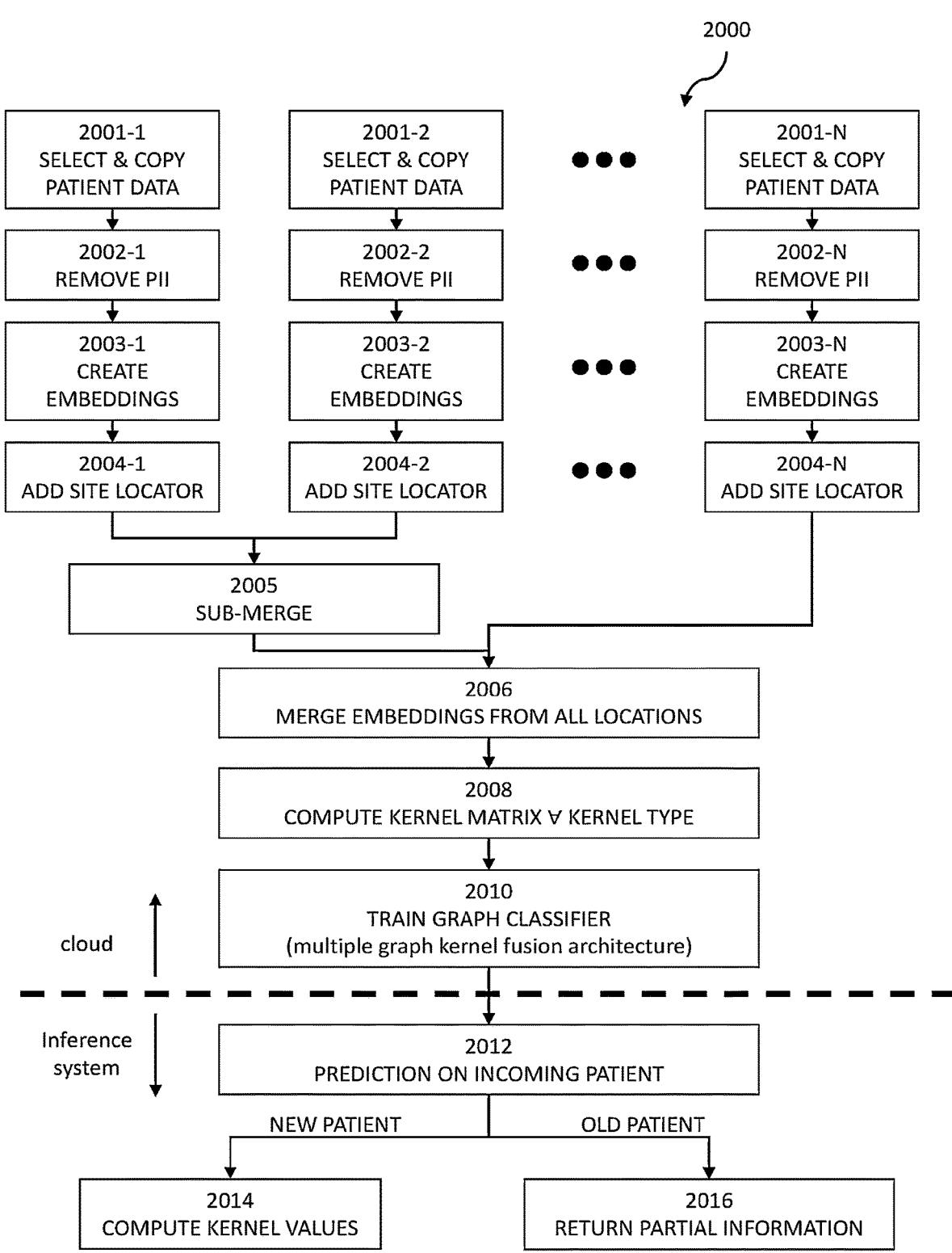
FIG. 20 is an exemplary flow diagram of a modified process including removal of personal identifying information (PII) from each patient during creation of an embedding of the patient record.

FIG. 20 illustrates an embodiment of the present application. A process 2000 of amalgamating or merging data from disparate sources is illustrated. The method starts with selecting data from a variety of different sources 2001-1, 2001-2, . . . 2001-N and creating a temporary copy of these data. The temporary copies of the healthcare records have any personally identifiable information (PII) removed from them at step 2002-1, 2002-2, . . . 2002-N. Then for each data source 2002-1, 2002-2, 2002-N, an embedding from each patient healthcare record is created at step 2003-1, 2003-2, . . . 2003-N. Thus, the embeddings 2003 (collectively) are created without any personally identifying information. In some embodiments, a site locator may be appended after the embeddings have been created at step 2004-1, 2004-2, . . . 2004-N. In other embodiments, the site locator may be appended before the embeddings are created.

These embeddings 2003 are created using any of the deep learning methods known in the art, preferably by pretrained deep learners. In one embodiment, the pretrained deep learner used to create the embeddings 2003 is specifically pretrained for medical or biological and/or clinical use, such as, but not limited to, Med-BERT, BioBERT or Bio_ClinicalBERT. Regardless of the particular deep learner used, in a preferred embodiment, the same deep learner is used across data sources 2002-1, 2002-2, . . . 2002-N to generate the embeddings 2003-1, 2003-2, . . . 2003-N. However, it is within the scope of this invention to use differing deep learners across data sources 2002-1, 2002-2, . . . 2002-N to generate the embeddings 2003-1, 2003-2, . . . 2003-N. Differences in embedding 2003-1, 2003-2, . . . 2003-N generated by using differing deep learners across data sources 2002-1, 2002-2, . . . 2002-N are learned and rectified when generating the sub-amalgamated 2005 and/or sub-merged embeddings for all locations 2006. After the embeddings are created from the temporary copies, the copies of the electronic healthcare records are deleted.

Each embedding 2003 also comprises a site locator 2004 for each record so that a record, if it happens to correspond most closely to a new patient's record, can be requested from that data source. In an embodiment, the site locators 2004 may be hierarchically organized to include the designation of a cluster of patient cohorts within the corresponding site. In some embodiments, the hierarchical organization is recursively generated to support a multi-level hierarchy. In an embodiment, the site locator 2004 is encrypted for additional security. In an embodiment, at step 2005, a sub-merger of at least two data sources may be created. In such an embodiment, the comparison with a new patient's embedding may take place with a sub-merger of other embeddings rather than the full amalgamation or merger from all locations. In such an embodiment, a user may wish to examine only the embeddings of other patients who live in the same area. At step 2006, the embeddings from the distributed data sources are merged to form a single database of embeddings. From this point onwards, the same process is followed as described in U.S. Pat. Nos. 11,238,966 and 11,410,763 to obtain an efficacious predicted treatment, which is also outlined elsewhere in this disclosure. Briefly, at step 2008, a kernel matrix is computed for each kernel type. In an embodiment, a temporal proximity kernel, a shortest path kernel, and a node kernel are calculated. At step 2010, a classifier is trained to predict the most likely outcome for a given treatment using, for example, a multiple graph kernel fusion architecture. At step 2012, a new patient's data are fed into the classifier, and the resulting prediction is returned. For a new patient at step 2014, kernel values are updated. For an old patient at step 2016, only partial information is returned.

Figure 23:
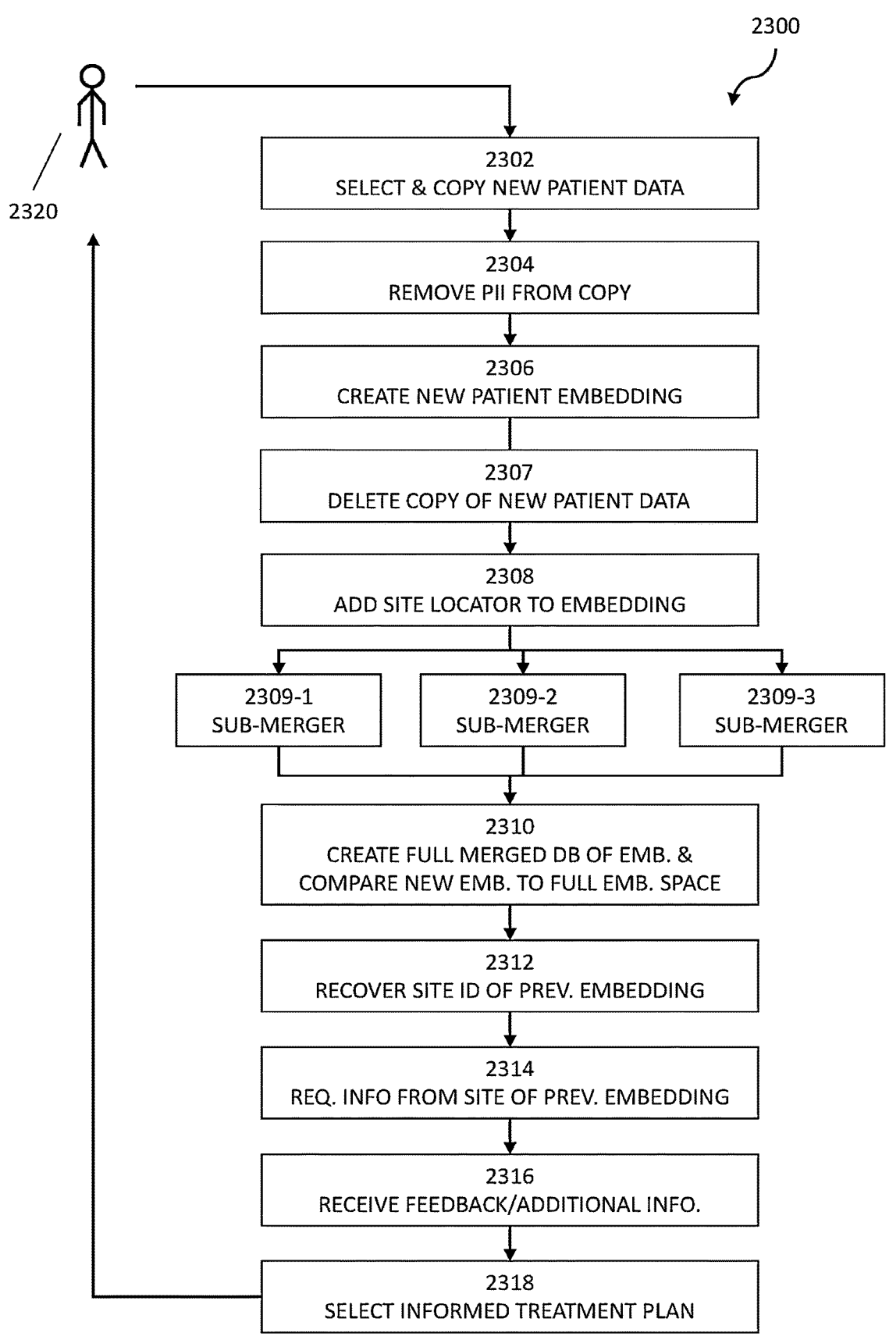
FIG. 23 shows an example of a process flow including feedback to the original patient.

Another embodiment is shown illustrated in FIG. 23. FIG. 23 shows an embodiment of the method 2300 including feedback to a new patient 2320. The new patient 2320 has met with their physician, and the new patient's data are collected in a new patient healthcare record, and a copy of this record is created 2302. This copy of the new patient health record 2302 may, of course, include older data related to the new patient 2320. The copy of the new patient's data 2302 has their personally identifiable information removed at step 2304. At step 2306, a new patient embedding is created. At step 2307 the copy of the new patient health record is deleted. At step 2308, a site locator may optionally be added to the embedding. The site locator may be appended to the new patient embedding after the embedding has been created. In an embodiment, a sub-merger of less than all the available data is made into a database at step 2309. In the example shown in FIG. 23, there are three sub-mergers 2309-1, 2309-2, and 2309-3, although any number may be made. In one embodiment, the sub-mergers may overlap. In one embodiment, the sub-mergers are pairwise disjoint. The new patient's embedding may be compared with the embeddings of the fully merged data set mapped in embedding space (also known as a semantic map or semantic mapping of all embeddings) at step 2310, as described elsewhere in this disclosure. In an embodiment, at step 2310 instead of comparing the new patient embedding with the embeddings of the full merger of embeddings, the method may compare the new patient's embedding with a sub-merger of embeddings at step 2309. For example, a user may wish to limit the possible embeddings only to those of other patients who have lived in the same area or were exposed to a particular environment or due to other reasons. At step 2310, a similar embedding of previous patient healthcare records is identified from the full merged dataset of embeddings, or from a sub-merger of embeddings, by comparing the new patient embedding with the other embeddings. In an embodiment, at step 2310, a previous embedding is identified that is that embedding which is most similar to the new patient embedding. In an embodiment, at step 2310, a previous embedding is identified by ranking each embedding of the merged database of embeddings by predicted treatment efficacy for the new patient embedding, and the embedding of the merged database of embeddings which yields the most efficacious predicted treatment is selected as the previous embedding.

At step 2312, after the previous embedding has been identified, the site locator for the previous embedding is extracted. At step 2314, the new patient's system may request, from the previous embedding's site, additional information about the previous patient or the previous patient's treatment. In an example, the system may request such additional information as may be relevant to confirm the diagnosis and the efficacy of the proposed treatment of the new patient 2320. The previous embedding's site may provide feedback at step 2316, in compliance with their own policies and regulations. At step 2318, the system may choose an informed treatment plan for the new patient 2320. This informed treatment plan is shared with the new patient 2320 or is shared with a third party such as a physician or an insurance company or shared with both the new patient and a third party. In an embodiment, the new patient may provide feedback to the system of the outcome of the treatment. For example, after being treated with a particular medication for a urinary tract infection, the patient reports back that the medication took 2 days to have any effect, but that it was successful in clearing up the infection.

Figure 24:
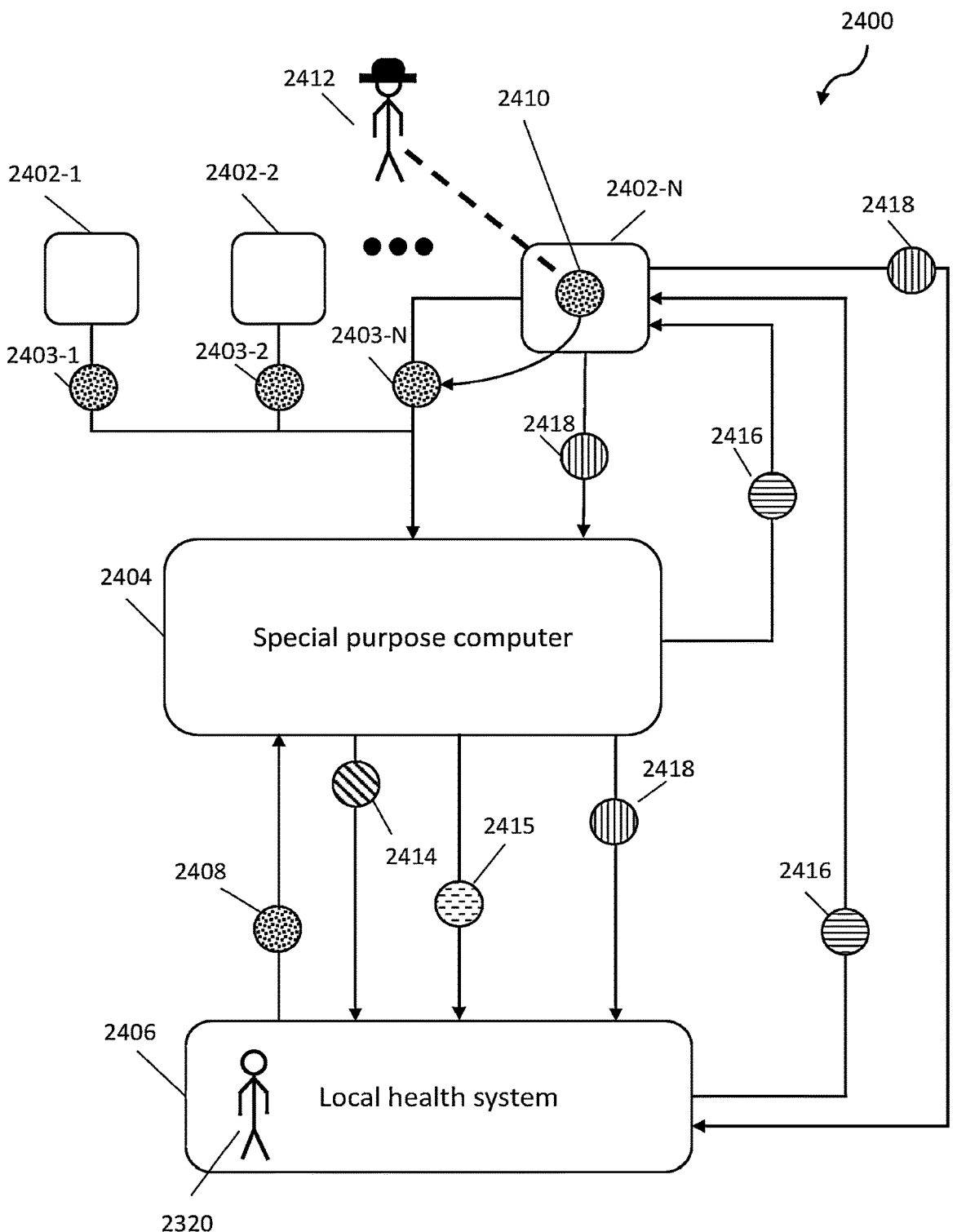
FIG. 24 illustrates an embodiment of the process of merging multiple electronic health records for identifying similar healthcare records.

FIG. 24 illustrates an embodiment of the overall process and the systems involved. The system 2400 may include the disparate electronic health record (EHR) systems (2402-1, 2402-2, . . . 2402-N) known collectively as 2402. These EHR systems 2402 may each perform the steps necessary to create an embedding of each of their patient records. That process may comprise, for each EHR, the steps of: creating a temporary copy of the EHR, removing any personally identifiable information from the temporary EHR copy, adding a site locator to the EHR copy, creating an embedding 2403 of the temporary EHR copy, storing the embedding, and deleting the temporary copy of the EHR. In an embodiment, the site locator may be added to or appended to the embedding after the embedding has been created. The set of embeddings 2403-1, 2403-2, . . . 2403-N from each of the EHR systems 2402-1, 2402-2, . . . 2402-N may then be shared with a special purpose computer 2404. These embeddings 2403 contain no personally identifiable information, and so, violate no regulations on the sharing of such information with outside parties without a patient's consent.

The special purpose computer 2404 may comprise a processor and electronic storage as described elsewhere in this disclosure. The special purpose computer 2404 can require additional processing power or memory or even specially designed processors to enable training of the models required. In an embodiment, the special purpose computer requires the use of an accelerator processor such as a tensor processor or a tensor streaming processor. The special purpose computer 2404 interacts with a local healthcare system 2406. The local healthcare system 2406 can be one of the systems 2402 which provide embeddings 2403 of patient records, but for purposes of illustrating this embodiment of the system and method the local healthcare system 2406 is represented in this figure as a separate entity.

The local healthcare system 2406 processes a new patient 2320. The new patient 2320 has their health record updated (or created if it is their first visit to the local healthcare system). The local healthcare system 2406, then applies the same process to create an embedding of the new patient healthcare record 2408 following the same procedure as the other EHR systems 2402: create temporary copy of the new patient EHR, remove any PII from the temporary copy, add a site locator to the copy, create an embedding 2408 from the copy, delete temporary copy of EHR, and share the new patient's EHR embedding 2408 with the special purpose computer 2404.

Once the special purpose computer 2404 receives the embedding of the new patient's EHR 2408, then the special purpose computer 2404 performs the method of comparing the new patient's EHR embedding 2408 with the merged database of embeddings 2403 which the special purpose computer 2404 has received from other EHR systems 2402. The special purpose computer 2404 identifies an embedding 2410 most similar to the new patient's embedding 2408 according to the methods detailed elsewhere in this disclosure such as those described in U.S. Pat. Nos. 11,238,966 and 11,410,763 and elsewhere in this disclosure. The deemed similar patient 2412 has healthcare records which, when converted to an embedding 2410 are the most similar to the new patient's embedding 2408. The special purpose computer 2404 then transmits a recommendation for treatment 2414 to the local healthcare system 2406 based on the identified most similar embedding 2410 from the merged set of embeddings. The special purpose computer 2404 may also transmit the site locator 2415 corresponding to that EHR system 2402-N from which the similar embedding 2410 originated.

When applying the process to identify a previous embedding 2410 to a new patient embedding 2408, a selected distance in embedding space defines the neighborhood in the embedding space around the new patient embedding 2408. If no embedding of the merged database of embeddings is found within this neighborhood of the new patient embedding, then the special purpose computer notifies the local healthcare system that no previous embedding 2410 has been identified which is located within the neighborhood of the new patient embedding 2408 in the embedding space given the selected distance. In the event that no previous embedding 2410 is identified, the special purpose computer 2404 reports the situation to the local health system 2406.

In FIG. 24, the EHR system is identified as 2402-N, but it could be any of the EHR systems 2402-1, 2402-2, etc. The local healthcare system 2406 or the special purpose computer 2404 may then place a request 2416 from the identified EHR system 2402-N for additional information 2418. The identified EHR system 2402-N may then respond with the requested additional information 2418 using the previous embedding 2410 and the merged database to identify relevant information such as the previous patient health record, treating physician or other information to be shared in accordance with the policy as determined by the identified EHR system 2402-N. In an alternative embodiment, the policy may prohibit disclosure of any portion of a patient health record. In such instances, the identified EHR system 2402-N may direct the treating medical personnel to a peer reviewed white paper or other abstracted medical research paper that describes conditions and treatment together with the results. This system 2400 may include an automatic request 2416 for additional information 2418 directly from the special purpose computer 2404, or the system 2400 may provide the site locator 2415 to the local healthcare system 2406 along with the treatment recommendation 2414. The local healthcare system 2406 then sends a request 2416 for the additional information 2418 from the identified EHR system 2402-N.

Computer Hardware and Systems

Figure 21:
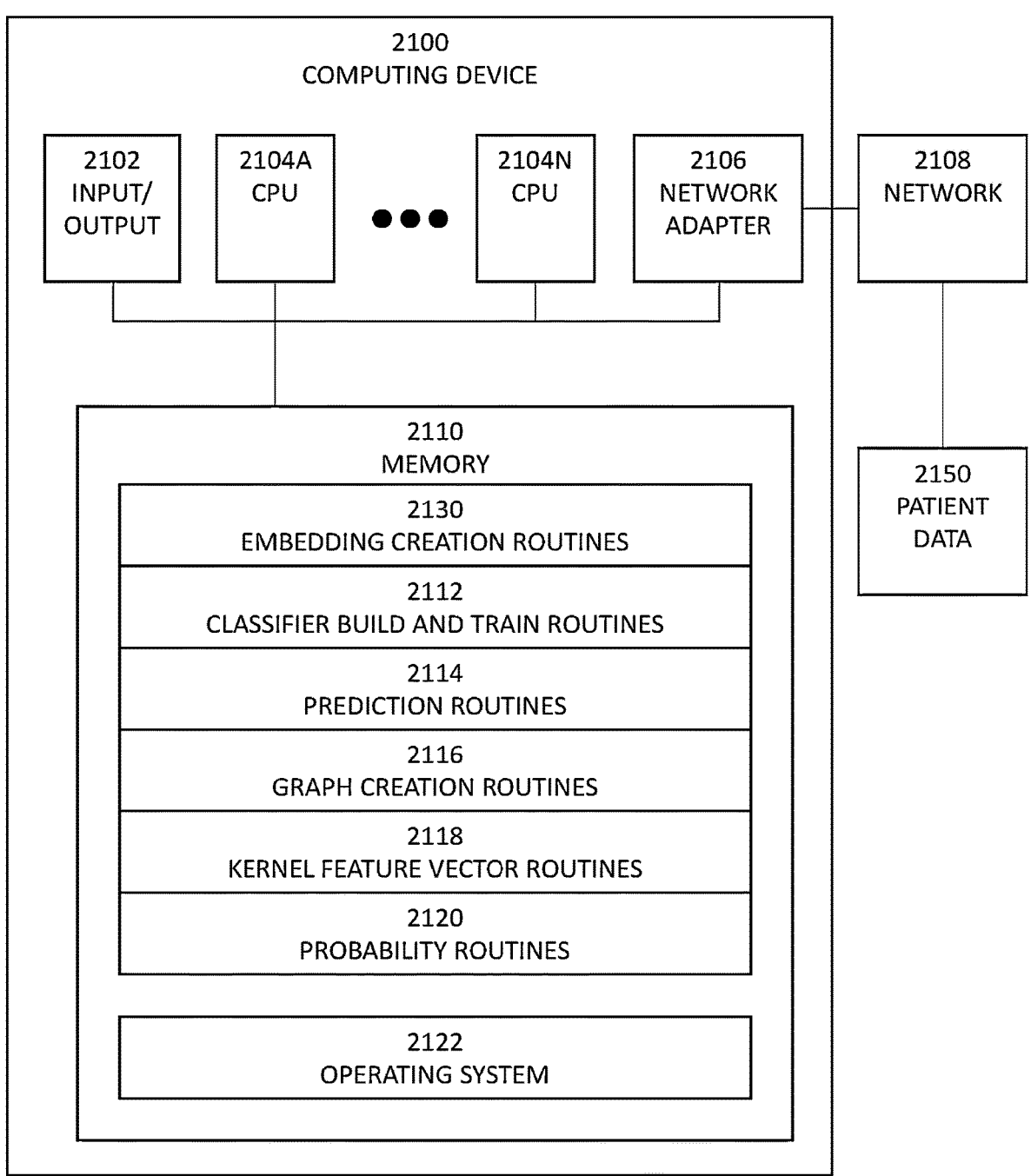
FIG. 21 is an exemplary block diagram of a computer device or system, in which processes involved in the embodiments described herein is implemented.

An exemplary block diagram of a computer system 2100, in which processes involved in the embodiments described herein is implemented, is shown in FIG. 21. In an embodiment the computer system 2100 may be a compute platform. Computer system 2100 is implemented using one or more programmed general-purpose computer systems, such as embedded processors, systems on a chip, personal computers, workstations, server systems, and minicomputers or mainframe computers, or in distributed, networked computing environments. In an embodiment, the computer system 2100 also comprises one or more special purpose processors (e.g., an accelerator or an accelerated processor) and may itself be a special purpose computer system. Computer system 2100 may include input/output circuitry 2102, one or more processors (CPUs) 2104A-2104N, network adapter 2106, and memory 2110. CPUs 2102A-2102N execute program instructions to carry out the functions of the present communications systems and methods. Typically, CPUs 2102A-2102N are one or more microprocessors, such as an INTEL CORE® processor, a GPU, a tensor multiplier core, or a tensor streaming processor, as described further below although the tensor streaming processor is a preferred accelerator. FIG. 21 illustrates an embodiment in which computer system 2100 is implemented as a single multi-processor computer system, in which multiple processors 2102A-2102N share system resources, such as memory 2110, input/output circuitry 2104, and a network adapter 2106. However, the present communications systems and methods also include embodiments in which computer system 2100 is implemented as a plurality of networked computer systems, which is single-processor computer systems, multi-processor computer systems, or a mix thereof.

Input/output circuitry 2102 provides the capability to input data to, or output data from, computer system 2100. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 2106 interfaces device 2100 with a network 2108. Network 2108 is any public or proprietary LAN or WAN, including, but not limited to the Internet.

Memory 2110 stores program instructions that are executed by, and data that are used and processed by, CPU

2104, or by CPUs 2104A, . . . 2104N, to perform the functions of computer system 2100. Memory 2110 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 2110 may vary depending upon the function that computer system 2100 is programmed to perform. In the example shown in FIG. 21, exemplary memory contents are shown representing routines and data for embodiments of the processes described above. However, one of skill in the art would recognize that these routines, along with the memory contents related to those routines, may not be included on one system or device, but rather is distributed among a plurality of systems or devices, based on well-known engineering considerations. The present communications systems and methods may include any and all such arrangements.

In the example shown in FIG. 21, memory 2110 includes embedding creation routines 2130, classifier build and train routines 2112, prediction routines 2114, graph creation routines 2116, kernel feature vector routines 2118, probability routines 2120, and an operating system 2122. Embedding creation routines 2130 includes software to remove or strip personally identifiable information and to create the vectors representing the stripped individual patient healthcare records. The embedding creation routines 2130 also includes a site locator in the vectors so that each embedding is tied to a specific healthcare provider location. Knowing the specific healthcare provider provides a critical feedback loop for the treating medical professional, who may be unable to implement a recommended treatment without more substantive basis for concluding that the prescription or treatment associated with the previous embedding is the optimum treatment for the current patient. More specifically, by providing the feedback loop, the medical professional for a current patient can request detailed clinical data from the medical professionals that confronted and apparently solved a similar condition in an earlier patient. This feature enables medical providers an efficient mechanism for eliminating "trial and error" responses to novel medical conditions where an optimal solution already exists.

Classifier build and train routines 2112 preferably include software to build and train a classifier with an MGKF framework for each type of disease, as described above. Prediction routines 2114 may include software to use the trained classifiers with an MGKF framework to perform prediction for each type of disease, as described above. Graph creation routines 2116 preferably include software to create patient graphs, as described above. Kernel feature vector routines 2118 preferably include software to calculate multiple types of kernel feature vectors. In an embodiment, these kernel feature vectors comprise a temporal proximity kernel, a shortest path kernel, and a node kernel, between each patient graph and all training examples, as described above. In other embodiments, other kernels may be chosen and the method is not limited to only three kernels. Probability routines 2120 may include software to generate a probability output using the MGKF with the same disease diagnosis type, as described above. Operating system 2122 may provide additional system functionality.

Figure 22:
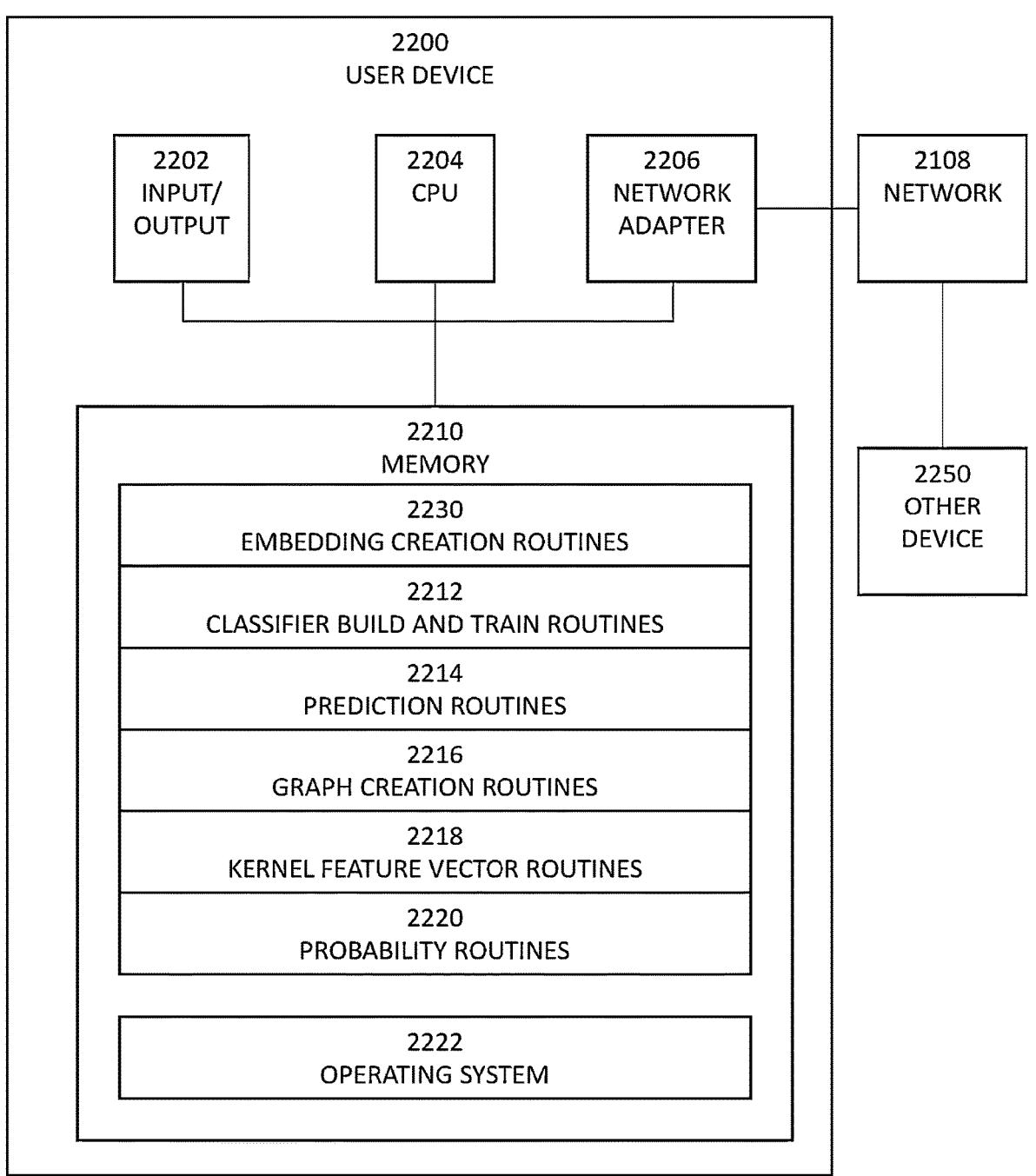
FIG. 22 is an exemplary block diagram of a user device.

A user device is illustrated schematically in FIG. 22. The user device 2200 comprises various input/output options 2202, for example keyboard, video screen, audio detector, speaker, mouse, trackball, etc. The user device 2200 further comprises a central processing unit 2204, a network adapter 2206 for connection to a network 2108. The central processing unit 2204 is coupled to the TSP to enable efficient execution of the classifier. Through the network 2108, the user device may be in contact with another device 2250 or with other devices, for instance a computing device 2100 which performs the calculations described in this disclosure. The user device 2200 further comprises memory 2210. The memory 2210 may include an operating system 2222 and various routines or algorithms. These routines preferably comprise embedding creation routines 2230, classifier build and train routines 2212, prediction routines 2214, graph creation routines 2216, kernel feature vector routines 2218, and probability routines 2220. In an embodiment, the user device is used to access a patient record stored on a remote device 2250. In an embodiment, the user device 2200 is used to add information to or update a patient record stored on a remote device 2250. In an embodiment, the user device 2200 receives the recommended or chosen treatment determined by the method described by this disclosure. The user device 2200 may comprise a mobile phone, a personal computer, a laptop, a notebook, or an electronic personal device. In an embodiment, the user device 2200 communicates with a remote device 2250 and the complex and resource intensive calculations may be performed on the remote device 2250. In this embodiment the remote device 2250 comprises, by way of example, a computing device 2100 with special processors (e.g., accelerators, tensor processors) or memory requirements designed to reduce the energy consumed during the calculations or designed to reduce the time required to complete the calculations. In an embodiment, the user device 2200 runs the trained classifier, but may lack the computing resources to train the classifier. In such an embodiment, the classifier training would occur only on the computing device 2100 rather than on the user device 2200.

The present systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention is a system, a method, and/or a computer program product at any possible technical detail level of integration. The computer program product includes a computer readable storage medium (or media) having computer readable program instructions thereon for causing a processor to carry out aspects of the present invention. The computer readable storage medium is a tangible device that can retain and store instructions for use by an instruction execution device.

The computer readable storage medium is, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The present systems and methods preferably include implementation on a system or systems that includes an accelerator system such as the GroqNode commercially available from Groq, Inc. of Mountain View, California. For example, the CPUs 2104 of the computing device 2100 may be one or more accelerators or one or more tensor streaming processors. The GroqNode includes a plurality of tensor streaming processors (TSPs), for example up to 4 TSPs that can be operated as a single core or as four individual accelerators for smaller vector sizes. Specific details of a TSP are more fully described in U.S. patent application Ser. No. 17/023,214 filed Mar. 16, 2021, which is incorporated herein by reference in its entirety for all purposes. Such a processor is significantly more energy efficient than a standard set of CPU or GPU cores with associated cached memory. The TSP is designed with a unique dataflow architecture that is more efficient than using a grid of cache-dependent cores coupled to a router-based communication grid. Thus, the present disclosure may also improve the energy efficiency relative to other analogous systems using machine learning. In particular, the TSP is a domain-specific architecture that accelerates deep learning workloads. The TSP is a functionally-sliced microarchitecture with memory units interleaved with vector and matrix functional units. This architecture takes advantage of dataflow locality of deep learning operations. The TSP is ideally suited to accelerate machine learning workloads that exhibit abundant data parallelism, which can be readily mapped to tensors in hardware. This deterministic processor with a stream programming model enables precise reasoning and control of hardware components to achieve good performance and power efficiency.

The TSP is designed to exploit parallelism inherent in machine-learning workloads including instruction-level parallelism, memory concurrency, data and model parallelism. It guarantees determinism by eliminating all reactive elements in the hardware, for example, arbiters and caches. The instruction ordering is entirely software controlled and the underlying hardware cannot reorder these events and each event must complete in a fixed amount of time. The TSP provides zero variance latency, low latency, high throughput at a batch size of one. The TSP functions as an accelerator working in conjunction with a host computer and external memory.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention is assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer is connected to the user's computer through any type of network, including a local area network (LAN) or a wide area network (WAN), or the connection is made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions are provided to a processor of a general-purpose computer, to an accelerator of a special purpose computer, or other programmable data processing apparatus to produce a machine, such that the instructions, which executed via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or that carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for computing a probable treatment efficacy, for use with a user device, comprising:

a processor;

an accelerator comprising a tensor streaming processor coupled to the processor; and memory accessible by the processor, wherein computer program instructions are stored in the memory and executable by the processor to perform:

creating a first plurality of embeddings from a first plurality of patient healthcare records using a pre-trained deep learning model, having had personally identifiable information removed and having added a first site locator, associated with a first site, wherein the first site locator is encrypted, to each embedding of the first plurality of embeddings;

creating a second plurality of embeddings from a second plurality of patient healthcare records using the pretrained deep learning model, having had personally identifiable information removed and having added a second site locator, associated with a second site, wherein the second site locator is encrypted, to each embedding of the second plurality of embeddings;

combining the first plurality of embeddings and the second plurality of embeddings into a merged database of embeddings;

receiving a new patient healthcare record for a new patient;

creating a new embedding from the new patient healthcare record using the pretrained deep learning model;

calculating a probable efficacy of a selected treatment of a plurality of treatments based on the merged database of embeddings, wherein the calculating is performed using the tensor streaming processor;

determining a recommended treatment, of the plurality of treatments, to be prescribed to the new patient based on the new embedding and on the calculated probable efficacy of the plurality of treatments, wherein the determining is performed using the tensor streaming processor; and reporting the recommended treatment to the user device.

2. The system of claim 1, wherein the first plurality of healthcare records is a copy of an original first plurality of healthcare records at the first site and wherein the second plurality of healthcare records is a copy of an original second plurality of healthcare records at the second site.

3. The system of claim 2, wherein the first plurality of healthcare records is deleted after the creation of the first plurality of embeddings and the second plurality of healthcare records is deleted after the creation of the second plurality of embeddings.

4. The system of claim 1, wherein calculating the probable efficacy of the selected treatment of the plurality of treatments based on the merged database of embeddings comprises:

capturing a plurality of features from each embedding of the merged database of embeddings; and training a classification model using a subset of the captured plurality of features of each embedding of the merged database of embeddings to predict the probable efficacy of the selected treatment, wherein the training is performed using the tensor streaming processor.

5. The system of claim 4, wherein the subset of the captured plurality of features is based on demographic information.

6. The system of claim 5, wherein the demographic information comprises at least one of geographical data, racial data, ethnic data, cultural data, gender-related data, or age-related data.

7. The system of claim 4, further comprising an accelerator coupled to the processor to assist in capturing the plurality of features and training the classification model to predict the probable efficacy of the selected treatment wherein the tensor streaming processor comprises one or more additional processors configured to function as a single core to assist the processor.

8. The system of claim 1, wherein the processor further performs the steps of:

receiving a site locator of an embedding of the merged database of embeddings most closely associated with the recommended treatment;

requesting additional information about the recommended treatment from a selected site identified by the selected site locator;

receiving the requested additional information from the selected site; and reporting to the user device the received additional information along with the recommended treatment.

9. The system of claim 1, wherein the processor further performs the step of receiving from the user device an acknowledgement when the recommended treatment was administered to the new patient.

10. The system of claim 1, wherein the processor further performs the step of receiving from the user device an indication of the efficacy of the recommended treatment.

11. A compute platform for calculating a probable treatment efficacy by creating a semantic map from a merged database of embeddings, wherein each embedding of the merged database of embeddings is created using a pretrained deep learning model and is associated with a site, an encrypted site locator, and a treatment of a plurality of treatments, the compute platform comprising:

a processor;

an accelerator comprising a tensor streaming processor coupled to the processor; and memory accessible by the processor, wherein computer program instructions are stored in the memory and executable by the processor to perform:

receiving a new embedding of a new patient's healthcare records from a new site, wherein the new embedding is created using the pretrained deep learning model;

determining a recommended treatment from the plurality of treatments to be recommended to the new patient by identifying a previous embedding of the merged database of embeddings similar to the new embedding, wherein the determining is performed using the tensor streaming processor;

reporting to the new site the recommended treatment of the plurality of treatments and the site locator associated with the previous embedding;

linking the new site to a site associated with the previous embedding based on the site locator associated with the previous embedding; and requesting that the site associated with the previous embedding provide additional information to the new site to substantiate that the recommended treatment is applicable to the new patient.

12. The compute platform of claim 11, wherein identifying the previous embedding of the merged database of embeddings comprises calculating a similarity of a plurality of similarities between the new embedding and each embedding of the merged database of embeddings and identifying the previous embedding as that embedding of the merged database of embeddings which has the greatest similarity of the plurality of similarities, and wherein if no similarity of the plurality of similarities exceeds a pre-defined threshold, then not identifying a previous embedding and reporting the lack of a previous embedding to the new site.

13. The compute platform of claim 11, wherein identifying the previous embedding of the new embedding comprises:

capturing a plurality of features from each embedding of the merged database of embeddings;

training a classification model using a subset of the captured plurality of features of each embedding of the merged database of embeddings, wherein the training is performed using the tensor streaming processor;

applying the trained classification model on the new embedding to determine a probability that each treatment of the plurality of treatments will be effective for the new patient; and identifying as the previous embedding of the merged database of embeddings that embedding of the merged database of embeddings which is associated with the highest probability that the associated treatment will be effective for the new patient.

14. The compute platform of claim 13, further comprising an accelerator coupled to the processor to assist in capturing the plurality of features and in training the classification model, wherein the tensor streaming processor comprises one or more additional processors configured to function as a single core to assist the processor.

15. A system, for use with a user device, for computing a probable treatment efficacy on a merged database of embeddings, wherein each embedding of the merged database of embeddings is created using a pretrained deep learning model and is associated with a site, an encrypted site locator, and a treatment of a plurality of treatments, comprising:

a processor;

memory accessible by the processor, wherein computer program instructions are stored in the memory and executable by the processor to perform:

capturing a plurality of features from each embedding of the merged database of embeddings;

training a classification model using a subset of the captured plurality of features of each embedding of the merged database of embeddings to determine a probable efficacy of a treatment of the plurality of treatments, wherein the training is performed using the tensor streaming processor, and sending the trained classification model to the user device;

receiving, at the user device, a new embedding associated with a new patient's healthcare records from a new site, wherein the new embedding is created using the pretrained deep learning model;

determining, at the user device, a recommended treatment of the plurality of treatments, to be prescribed to the new patient based on the trained classification model and the new embedding;

determining, at the user device, a recommended site associated with the recommended treatment of the plurality of treatments; and establishing, at the user device, a connection to the recommended site to retrieve validation information to support the recommended treatment.

16. The system of claim 15, wherein receiving the new embedding comprises the steps of:

receiving, at the user device, a copy of the new patient's healthcare records from the new site;

creating, at the user device, the new embedding based on the copy of the new patient's healthcare records, wherein the creating uses the pretrained deep learning model; and deleting, at the user device, the received copy of the new patient's healthcare records.

17. A system for creating a merged database of embeddings of patient healthcare records for use with a user device comprising:

a processor;

memory accessible by the processor, wherein computer program instructions are stored in the memory and executable by the processor to perform:

removing personally identifiable information from each patient healthcare record of a first plurality of patient healthcare records from a first site;

removing personally identifiable information from each patient healthcare record of a second plurality of patient healthcare records from a second site;

creating a first plurality of embeddings from the first plurality of patient healthcare records using a pretrained deep learning model and adding a first site locator, associated with the first site, wherein the first site locator is encrypted, to each embedding of the first plurality of embeddings;

creating a second plurality of embeddings from the second plurality of patient healthcare records using the pretrained deep learning model and adding a second site locator, associated with the second site, wherein the second site locator is encrypted, to each embedding of the second plurality of embeddings;

combining the first plurality of embeddings and the second plurality of embeddings into a merged database of embeddings;

capturing a plurality of features from each embedding of the merged database of embeddings;

training a classification model using a subset of the captured plurality of features of each embedding of the merged database of embeddings to determine the probable efficacy of each treatment of the plurality of treatments, wherein the training is performed using the tensor streaming processor; and transmitting the trained classification model to the user device.

18. The system of claim 17, wherein the first plurality of healthcare records is a copy of an original first plurality of healthcare records from the first site and wherein the second plurality of healthcare records is a copy of an original second plurality of healthcare records from the second site.

19. The system of claim 17, further comprising, at the user device:

receiving the trained classification model;

receiving a new patient healthcare record;

converting the new patient healthcare record into a new embedding, wherein the converting uses the pretrained deep learning model;

determining a recommended treatment of the plurality of treatments to be prescribed to the new patient based on the trained classification model and the new embedding;

determining a recommended site associated with the recommended treatment of the plurality of treatments;

establishing a connection to the recommended site to retrieve validation information in support of the recommended treatment; and displaying the recommended treatment and the validation information in support of the recommended treatment.

20. The system of claim 19, further comprising transmitting, from the user device to the processor, an acknowledgement when the recommended treatment was administered to the new patient.

21. The system of claim 19, further comprising transmitting, from the user device to the processor, an indication of the efficacy of the recommended treatment.

* * * * *